(12) United States Patent
Angibaud et al.

(10) Patent No.: US 8,138,198 B2
(45) Date of Patent: Mar. 20, 2012

(54) SUBSTITUTED AMINOPROPENYL PIPERIDINE OR MORPHOLINE DERIVATIVES AS NOVEL INHIBITORS OF HISTONE DEACETYLASE

(76) Inventors: Patrick René Angibaud, Fontaine-Bellenger (FR); Laurence Françoise Bernadette Marconnet-Decrane, Romilly sur Andelle (FR); Sven Franciscus Anna Van Brandt, Nijlen (BE); Isabelle Noëlle Constance Pilatte, Louviers (FR)

(*) Notice: Subject to any disclaimer, the term of this patent is extended or adjusted under 35 U.S.C. 154(b) by 964 days.

(21) Appl. No.: 11/914,208

(22) PCT Filed: May 16, 2006

(86) PCT No.: PCT/EP2006/062324
§ 371 (c)(1),
(2), (4) Date: Nov. 12, 2007

(87) PCT Pub. No.: WO2006/122926
PCT Pub. Date: Nov. 23, 2006

(65) Prior Publication Data
US 2009/0221580 A1    Sep. 3, 2009

(30) Foreign Application Priority Data
May 18, 2005   (EP) .................................... 05104155

(51) Int. Cl.
*A01N 43/54* (2006.01)
*A61K 31/505* (2006.01)
*C07D 419/00* (2006.01)

(52) U.S. Cl. ........................ 514/275; 544/332
(58) Field of Classification Search .................. 514/275; 544/332
See application file for complete search history.

(56) References Cited

U.S. PATENT DOCUMENTS

| | | |
|---|---|---|
| 3,331,843 A | 7/1967 | Tomcufcik et al. |
| 3,966,743 A | 6/1976 | Berger et al. |
| 4,049,811 A | 9/1977 | Berger et al. |
| 4,348,401 A | 9/1982 | Friebe et al. |
| 4,455,422 A | 6/1984 | Banno et al. |
| 5,025,012 A | 6/1991 | Miura et al. |
| 5,147,876 A | 9/1992 | Mizuchi et al. |
| 5,338,738 A | 8/1994 | Matson et al. |
| 5,342,846 A | 8/1994 | Singh et al. |
| 5,780,454 A | 7/1998 | Adams et al. |
| 5,789,412 A | 8/1998 | Halazy et al. |
| 5,952,349 A | 9/1999 | Asberom et al. |
| 6,066,730 A | 5/2000 | Adams et al. |
| 6,083,903 A | 7/2000 | Adams et al. |
| 6,294,538 B1 | 9/2001 | Mylari |
| 6,518,283 B1 | 2/2003 | Langham et al. |
| 7,205,304 B2 | 4/2007 | Van Emelen et al. |
| 7,446,109 B2 | 11/2008 | Van Emelen et al. |
| 7,501,417 B2 | 3/2009 | Van Emelen et al. |
| 7,541,369 B2 | 6/2009 | Angibaud et al. |
| 7,592,450 B2 | 9/2009 | Van Emelen |
| 7,615,553 B2 | 11/2009 | Van Emelen et al. |
| 7,704,998 B2 | 4/2010 | Van Emelen et al. |
| 7,709,487 B2 | 5/2010 | Van Emelen et al. |
| 7,767,679 B2 | 8/2010 | Van Emelen et al. |
| 7,816,363 B2 | 10/2010 | Angibaud et al. |
| 7,834,011 B2 | 11/2010 | Roux et al. |
| 7,834,025 B2 | 11/2010 | Angibaud et al. |
| 7,884,105 B2 | 2/2011 | Van Emelen |
| 7,888,360 B2 | 2/2011 | Angibaud et al. |
| 2002/0032195 A1 | 3/2002 | Breitfelder et al. |
| 2004/0248897 A1 | 12/2004 | Priepke et al. |
| 2005/0080258 A1 | 4/2005 | Davis et al. |
| 2005/0096468 A1 | 5/2005 | Van Emelen et al. |
| 2005/0107384 A1 | 5/2005 | Angibaud et al. |
| 2005/0171347 A1 | 8/2005 | Van Emelen et al. |
| 2005/0197336 A1 | 9/2005 | Anandan et al. |
| 2005/0222414 A1 | 10/2005 | Van Emelen et al. |
| 2007/0135424 A1 | 6/2007 | Van Brandt et al. |
| 2008/0132459 A1 | 6/2008 | Moradei et al. |

(Continued)

FOREIGN PATENT DOCUMENTS

CA   2 491 131 A1   1/2004
(Continued)

OTHER PUBLICATIONS

Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
In the U.S. Appl. No. 10/506,998 Non-Final Office Action dated Oct. 2, 2008, 5 pages.
In the U.S. Appl. No. 10/506,998 Non-Final Office Action dated Jun. 19, 2007, 7 pages.

(Continued)

*Primary Examiner* — San-Ming Hui
*Assistant Examiner* — Paul Zarek
(74) *Attorney, Agent, or Firm* — Rajiv Shah, Esquire; Johnson & Johnson

(57) ABSTRACT

This invention comprises the novel compounds of formula (I) wherein $R^1$, $R^2$, $R^3$, $R^4$, X and Y have defined meanings, having histone deacetylase inhibiting enzymatic activity; their preparation, compositions containing them and their use as a medicine.

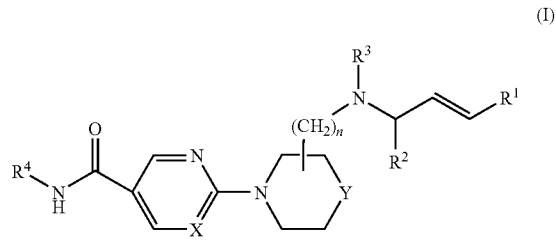

(I)

14 Claims, No Drawings

U.S. PATENT DOCUMENTS

| | | |
|---|---|---|
| 2008/0255140 A1 | 10/2008 | Van Emelen |
| 2009/0005393 A1 | 1/2009 | Angibaud et al. |
| 2009/0018152 A1 | 1/2009 | Angibaud et al. |
| 2009/0018153 A1 | 1/2009 | Angibaud et al. |
| 2009/0023726 A1 | 1/2009 | Roux et al. |
| 2009/0036463 A1 | 2/2009 | Angibaud et al. |
| 2009/0042920 A1 | 2/2009 | Van Emelen et al. |
| 2009/0124646 A1 | 5/2009 | Verdonck et al. |
| 2009/0143401 A1 | 6/2009 | Marconnet-Decrane et al. |
| 2009/0170836 A1 | 7/2009 | Angibaud et al. |
| 2009/0170881 A1 | 7/2009 | Angibaud et al. |
| 2009/0221580 A1 | 9/2009 | Angibaud et al. |
| 2009/0227558 A1 | 9/2009 | Angibaud et al. |
| 2009/0270419 A1 | 10/2009 | Arts et al. |
| 2010/0009988 A1 | 1/2010 | Van Emelen |
| 2010/0010004 A1 | 1/2010 | Van Emelen et al. |
| 2010/0048588 A1 | 2/2010 | Van Emelen et al. |
| 2010/0160321 A1 | 6/2010 | Ten Holte et al. |
| 2010/0222574 A1 | 9/2010 | Rombouts et al. |
| 2010/0234353 A1 | 9/2010 | Van Emelen et al. |
| 2010/0240639 A1 | 9/2010 | Van Emelen et al. |

FOREIGN PATENT DOCUMENTS

| | | | |
|---|---|---|---|
| CA | 2 518 950 A1 | 2/2005 | |
| DE | 042 28 792 A1 | 3/1994 | |
| DE | 102 33 412 A1 | 2/2004 | |
| EP | 0 076 530 B1 | 12/1985 | |
| EP | 0 188 094 B1 | 3/1992 | |
| EP | 0 788 360 B1 | 8/1997 | |
| EP | 0 827 742 A1 | 3/1998 | |
| EP | 1 312 609 B1 | 5/2003 | |
| EP | 1 472 216 A2 | 11/2004 | |
| EP | 1 485 353 A1 | 12/2004 | |
| EP | 1 495 002 A1 | 1/2005 | |
| EP | 1 523 470 A1 | 4/2005 | |
| EP | 1 525 199 A1 | 4/2005 | |
| EP | 1 572 626 A1 | 9/2005 | |
| EP | 1 583 736 A1 | 10/2005 | |
| EP | 1 585 735 A1 | 10/2005 | |
| EP | 1 592 667 A2 | 11/2005 | |
| EP | 1 608 628 A2 | 12/2005 | |
| EP | 1 613 622 A1 | 1/2006 | |
| EP | 1 627 880 A1 | 2/2006 | |
| EP | 1 663 953 A1 | 6/2006 | |
| EP | 1 501 508 B1 | 2/2007 | |
| EP | 1 581 484 B1 | 7/2007 | |
| EP | 1 592 665 A4 | 7/2007 | |
| EP | 1 685 094 A4 | 8/2007 | |
| EP | 1 485 354 B1 | 5/2008 | |
| EP | 1 485 365 B1 | 5/2008 | |
| EP | 1 485 348 B1 | 6/2008 | |
| EP | 1 485 378 B1 | 6/2008 | |
| EP | 1 492 534 B1 | 6/2008 | |
| EP | 1 485 364 B1 | 3/2009 | |
| EP | 1 485 370 B1 | 3/2009 | |
| EP | 1 682 538 A4 | 5/2009 | |
| EP | 1 611 088 B1 | 6/2009 | |
| EP | 1 590 340 B1 | 4/2010 | |
| EP | 1 673 349 B1 | 6/2010 | |
| EP | 1 485 099 B1 | 7/2010 | |
| ES | 2 104 509 A1 | 10/1997 | |
| GB | 0 901 749 A | 7/1962 | |
| GB | 1 345 872 A | 2/1974 | |
| WO | WO-94/25437 | 11/1994 | |
| WO | WO-96/13266 | 5/1996 | |
| WO | WO-97/23216 | 7/1997 | |
| WO | WO-98/55449 A1 | 12/1998 | |
| WO | WO-00/26203 A1 | 5/2000 | |
| WO | WO-00/35855 A1 | 6/2000 | |
| WO | WO-00/52001 A1 | 9/2000 | |
| WO | WO-00/71516 A2 | 11/2000 | |
| WO | WO-01/38322 A1 | 5/2001 | |
| WO | WO-01/70675 A2 | 9/2001 | |
| WO | WO-02/00651 | 1/2002 | |
| WO | WO-02/18335 | 3/2002 | |
| WO | WO-02/42271 | 5/2002 | |
| WO | WO-03/000653 A1 | 1/2003 | |
| WO | WO-03/011851 A2 | 2/2003 | |
| WO | WO-03/035855 A1 | 5/2003 | |
| WO | WO 03/066579 | * | 8/2003 |
| WO | WO-03/075929 A1 | 9/2003 | |
| WO | WO-03/076395 A1 | 9/2003 | |
| WO | WO-03/076400 A1 | 9/2003 | |
| WO | WO-03/076401 A1 | 9/2003 | |
| WO | WO-03/076421 A1 | 9/2003 | |
| WO | WO-03/076422 A1 | 9/2003 | |
| WO | WO-03/076430 A1 | 9/2003 | |
| WO | WO 03/076438 | * | 9/2003 |
| WO | WO-03/082288 A1 | 10/2003 | |
| WO | WO-03/087057 A1 | 10/2003 | |
| WO | WO-2004/009536 A1 | 1/2004 | |
| WO | WO-2004/013130 A1 | 2/2004 | |
| WO | WO-2004/056748 A1 | 7/2004 | |
| WO | WO-2004/063146 A1 | 7/2004 | |
| WO | WO-2004/063169 A1 | 7/2004 | |
| WO | WO-2004/065354 A1 | 8/2004 | |
| WO | WO-2004/069803 A2 | 8/2004 | |
| WO | WO-2004/069823 A1 | 8/2004 | |
| WO | WO-2004/071400 A2 | 8/2004 | |
| WO | WO-2004/072047 A1 | 8/2004 | |
| WO | WO-2004/082638 A2 | 9/2004 | |
| WO | WO-2004/087693 A1 | 10/2004 | |
| WO | WO-2004/092115 A2 | 10/2004 | |
| WO | WO-2005/028447 A1 | 3/2005 | |
| WO | WO-2005/030704 A1 | 4/2005 | |
| WO | WO-2005/030705 A1 | 4/2005 | |
| WO | WO-2005/040101 A1 | 5/2005 | |
| WO | WO-2005/075469 A1 | 8/2005 | |
| WO | WO-2005/086898 A2 | 9/2005 | |
| WO | WO-2005/092899 A1 | 10/2005 | |
| WO | WO-2006/010749 A1 | 2/2006 | |
| WO | WO-2006/010750 A1 | 2/2006 | |
| WO | WO-2006/122926 A1 | 11/2006 | |
| WO | WO-2006/136553 A1 | 12/2006 | |
| WO | WO-2007/016532 A2 | 2/2007 | |
| WO | WO-2007/048767 A1 | 5/2007 | |
| WO | WO-2007/082873 A1 | 7/2007 | |
| WO | WO-2007/082874 A1 | 7/2007 | |
| WO | WO-2007/082876 A1 | 7/2007 | |
| WO | WO-2007/082878 A1 | 7/2007 | |
| WO | WO-2007/082880 A1 | 7/2007 | |
| WO | WO-2007/082882 A1 | 7/2007 | |
| WO | WO-2008/031820 A2 | 3/2008 | |

OTHER PUBLICATIONS

In the U.S. Appl. No. 10/507,084 Non-Final Office Action dated Jul. 22, 2008, 5 pages.

In the U.S. Appl. No. 10/507,084 Non-Final Office Action dated Feb. 25, 2008, 5 pages.

In the U.S. Appl. No. 10/507,084 Non-Final Office Action dated Jun. 1, 2007, 7 pages.

In the U.S. Appl. No. 10/507,159 Non-Final Office Action dated Jun. 25, 2009, 7 pages.

In the U.S. Appl. No. 10/507,271 Final Office Action dated May 2, 2008, 5 pages.

In the U.S. Appl. No. 10/507,271 Non-Final Office Action dated Jul. 25, 2007, 12 pages.

In the U.S. Appl. No. 10/507,784 Non-Final Office Action dated Feb. 13, 2008, 5 pages.

In the U.S. Appl. No. 10/507,784 Non-Final Office Action dated Sep. 24, 2007, 5 pages.

In the U.S. Appl. No. 10/507,784 Non-Final Office Action dated Apr. 6, 2007, 13 pages.

In the U.S. Appl. No. 10/507,785 Non-Final Office Action dated May 13, 2008, 6 pages.

In the U.S. Appl. No. 10/507,785 Non-Final Office Action dated Jul. 19, 2007, 16 pages.

In the U.S. Appl. No. 10/507,788 Non-Final Office Action dated Oct. 19, 2007, 17 pages.

In the U.S. Appl. No. 11/626,215 *Ex-Parte* Quayle Action dated Apr. 2, 2009, 6 pages.

In the U.S. Appl. No. 11/626,215 Non-Final Office Action dated Jul. 9, 2008, 14 pages.

In the U.S. Appl. No. 11/917,999 Non-Final Office Action dated Sep. 15, 2010, 13 pages.
In the U.S. Appl. No. 11/917,999 Final Office Action dated Feb. 24, 2011, 15 pages.
In the U.S. Appl. No. 12/090,771 Advisory Action dated Dec. 2, 2009, 3 pages.
In the U.S. Appl. No. 12/090,771 Final Office Action dated Aug. 24, 2009, 6 pages.
In the U.S. Appl. No. 12/090,771 Non-Final Office Action dated Dec. 23, 2008, 11 pages.
In the U.S. Appl. No. 12/160,120 Non-Final Office Action dated Sep. 30, 2009, 13 pages.
In the U.S. Appl. No. 12/160,133 Non-Final Office Action dated Sep. 29, 2009, 12 pages.
In the U.S. Appl. No. 12/160,140 Non-Final Office Action dated Aug. 9, 2010, 6 pages.
In the U.S. Appl. No. 12/160,140 Non-Final Office Action dated Sep. 30, 2009, 14 pages.
In the U.S. Appl. No. 12/160,156 Non-Final Office Action dated Sep. 29, 2009, 13 pages.
In the U.S. Appl. No. 12/160,221 Non-Final Office Action dated Jan. 19, 2010, 7 pages.
In the U.S. Appl. No. 12/233,977 Non-Final Office Action dated Jun. 3, 2010, 6 pages.
In the U.S. Appl. No. 12/360,139 Non-Final Office Action dated Aug. 19, 2010, 22 pages.
In the U.S. Appl. No. 12/360,139 Final Office Action dated Mar. 17, 2011, 8 pages.
In the U.S. Appl. No. 12/372,801 Non-Final Office Action dated Jun. 10, 2010, 5 pages.
In the U.S. Appl. No. 12/372,801 Final Office Action dated Nov. 29, 2010, 6 pages.
In the U.S. Appl. No. 12/372,801 Non-Final Office Action dated Dec. 10, 2009, 7 pages.
In the U.S. Appl. No. 12/539,682 Non-Final Office Action dated Aug. 17, 2010, 8 pages.
In the U.S. Appl. No. 12/539,682 Final Office Action dated Feb. 1, 2011, 11 pages.
In the U.S. Appl. No. 11/572,563 Advisory Action dated Jun. 3, 2011, 3 pages.
In the U.S. Appl. No. 11/572,563 Final Office Action dated Mar. 3, 2011, 5 pages.
In the U.S. Appl. No. 11/572,563 Final Office Action dated Jul. 9, 2010, 8 pages.
In the U.S. Appl. No. 11/572,563 Non-Final Office Action dated Sep. 29, 2009, 14 pages.
In the U.S. Appl. No. 11/668,906 Non-Final Office Action dated Feb. 20, 2009, 8 pages.
In the U.S. Appl. No. 12/160,124 Non-Final Office Action dated Mar. 25, 2011, 12 pages.
In the U.S. Appl. No. 10/507,708 Non-Final Office Action dated Nov. 23, 2005, 15 pages.
In the U.S. Appl. No. 10/507,708 Final Office Action dated May 8, 2006, 11 pages.
In the U.S. Appl. No. 11/926,759 Non-Final Office Action dated May 13, 2009, 9 pages.
In the U.S. Appl. No. 12/759,256 Non-Final Office Action dated Jan. 7, 2011, 7 pages.
Acharya et al., "Rational Development of Histone Deacetylase Inhibitors as Anticancer Agents: A Review," *Molecular Pharmacology*, 2005; 68(4):917-932.
Angibaud et al., "Discovery of Pyrimidyl-5-Hydroxamic Acids as New Potent Histone Deacetylase Inhibitors," *European Journal of Medicinal Chemistry*, 2005; 40:597-606.
Archibald et al., "Benzamidopiperidines 3. Carbocyclic Derivatives Related to Indoramin," *Journal of Medicinal Chemistry*, 1974; 17(7):739-744.
Bali et al., "Mechanisms Underlying Hydroxamic Acid Analogue (HA) Histone Deacetylase (HDAC) Inhibitors (HDIs)—Induced Apoptosis: New Role of HDAC6 Inhibition, Acetylation and Inhibition of hsp90 and Depletion of Pro-Growth and ProSurvival Oncoproteins," *Proceedings of the American Association for Cancer Research Annual Meetings*, 2005; 46(#3268):769-770.

Bali et al., "Inhibition of Histone Deacetylase 6 Acetylates and Disrupts the Chaperone Function of Heat Shock Protein 90," *Journal of Biological Chemistry*, 2005, 280(29):26729-26734.
Bali et al., "A Combination of Histone Deacetylase Inhibitor LAQ 824 and the FLT-3 Kinase Inhibitor PKC412 is Highly Active Against Human AML Cells with Constitutively Active Mutant FLT-3 Tyrosine Kinase," *Blood*, 2003; 102(11):96a-97a.
Banker et al., "Prodrugs," Modern pharmaceuticals, *Marcel Dekker, Inc.*, 3rd Ed. 1996; p. 596.
Bertino et al., "Principles of Cancer," *Cecil's Textbook of Medicine*, 2000; 21$^{st}$ Edition, vol. 1:1060-1074.
Birch et al., "N-Substituted (2, 3-Dihydro-1, 4-benzodioxin-2-yl)methylamine Derivatives as D2 Antagonists/5-HT1A Partial Agonists with Potential as Atypical Antipsychotic Agents," *J. Med. Chem.*, 1999; 42:3342-3355.
Blagosklonny et al., "Histone Deacetylase Inhibits all Induce P21 but Differentially Cause Tubulin Acetylation, Mitotic Arrest, and Cytotoxicity," *Molecular Cancer Therapeutics*, 2002; 1(11):937-941.
Catley et al., "Novel Hydroxamic Acid-Derived HDAC Inhibitor LBH589 Potently Activates Intrinsic and Induces Tubulin Hyperacetylation in Multiple Myeloma," *Blood*, 2005; 106(11):Abstract 1578; p. 435A.
Chen et al., "A Short and General Approach to the Synthesis of Styryllactones: (+)-Goniodiol, its Acetates and β-Trifluoromethyl Derivative, (+)-7-*epi*-Goniodiol and (+)-9-Deoxygoniopypyrone," *SYNLETT*, 2002; 8:1265-1268.
Chou et al., "Chemotherapeutic Synergism, Potentiation and Antagonism," *Encyclopedia of Human Biology*, 1991; 2:371-379.
Chou et al., "Quantitative Analysis of Dose-Effect Relationships: The Combined Effects of Multiple Drugs or Enzyme Inhibitors," *Adv. Enzyme Regul.*, 1984; 22: 27-55.
Chou et al., "The Median-Effect Principle and the Combination Index for Quantitation of Synergism and Antagonism," *Synergism and Antagonism in Chemotherapy*, 1991; pp. 60-103.
Chou et al., "Computerized Quantitation of Synergism and Antagonism of Taxol, Topotecan, and Cisplatin Against Human Teratocarcinoma Cell Growth: A Rational Approach to Clinical Protocol Design," *J. Natl. Cancer Inst.*, 1994; 86(20):1517-1524.
Dankwardt, et al., "Solid Phase Synthesis of Aryl and Benzylpiperazines and their Applications in Combinatorial Chemistry," *Tetrahedron Letters*, 1995; 36(28):4923-4926.
Dermer et al., "Another Anniversary for the War on Cancer," *BioTechnology*, 1994; 12:320.
Finney, D.J., "Probit Analyses,—A Statistical Treatment of the Sigmoid Response Curve," Graded Responses, Cambridge University Press, 1962; 2nd Ed. Chapter 10.
Finnin et al., "Structure of a Histone Deacetylase Homologue Bound to the TSA and SAHA Inhibitors," *Nature*, 1999; 401:188-193.
Foks et al., "Investigations on Pyrazine Derivatives Part II, Synthesis and Tuberculostatic Action of Some 6-Alkylaminopyrazine-2-carboxylic Acids," *Dissert. Parm. Pharmacol.*, 1972; 24:576-583.
Foks et al., "Studies on Pyrazine Derivatives Part X, Synthesis and Tuberculostatic Activity of some 6-Cyanolamino-6-Imidazolyl- and Triazolypyrazine-2-Carboxylic Acids Derivatives," *Pol. J. Pharmcol Pharm.*, 1978; 30:105-111.
Freshney et al., "Culture of Animal Cells, A Manual of Basic Technique," Alan R Liss, Inc. 1983 New York, p. 1-6.
Glaser, "HDAC Inhibitors: Clinical Update and Mechanism-Based Potential," *Biochemical Pharmacology*, 2007; 74(5):659-671.
Golub et al., "Molecular Classification of Cancer: Class Discovery and Class Prediction by Gene Expression Monitoring," *Science*, 1999; 286:531-537.
Gorrod et al, "The Metabolism of *N*-Ethyl-*N*-methylaniline by Rabbit Liver Microsomes: The Measurement of Metabolites by Gas-Liquid Chromatography," *Xenobiotica*, 1975; 5(8):453-462.
Hideshima et al., "Small-Molecule Inhibition of Proteasome and Aggresome Function Induces Synergistic Antitumor Activity in Multiple Myeloma," *PNAS*, 2005; 102(24):8567-8572.
Horton et al., "Bortezomib Interactions with Chemotherapy Agents in Acute Leukemia In Vitro," *Cancer Chemotherapy and Pharmacology*, 2006; 58(1):13-23.

*Internal Medicine*, 4th Edition, Editor-in-Chief Jay Stein, Chapters 71-72, pp. 699-715.
Irikura et al., "Absorption, Excretion, and Metabolism of 1-(ρ-aminobenzoyl)-4-(3, 4, 5-trimethoxybenzamido)piperidine (KU-55)," *Pharmacometrics*, 1973; 7(7):985-990. (With English-language Abstract).
Khuthier et al., "Studies of Tertiary Amine Oxides, 9. Thermal Rearrangement of 1-(4-Substituted-phenyl)piperidine *N*-Oxides to the Corresponding *N*-Hydroxlmines," *J. Org. Chem*, 1987: 52:1710-1713.
Kristeleit et al., "Histone Modification Enzymes: Novel Targets for Cancer Drugs," *Expert Opin. Emerg. Drugs*, 2004; 9(1):135-154.
Lentzsch et al., "Combination of Proteasome Inhibitor PS 341 with Histone Acetylase Inhibitor (HDAC) PXD 101 Shows Superior Anti-Myeloma Activity and Inhibits Osteoclastogenesis," *Blood Poster Session*, 2005; 106(Abstract 2488):p. 1.
Mai et al., Histone Deacetylation in Epigenetics: an Attractive Target for Anticancer Therapy, *Medicinal Research Reviews*, 2005; 25(3):261-309.
Marks et al., "Histone Deacetylases and Cancer: Cause and Therapies," *Nature Reviews: Cancer*, 2001; 1(3):194-202.
Mitsiades et al., Transcriptional Signature of Histone Deacetylase Inhibition in Multiple Myeloma: Biological and Clinical Implications, *PNAS*, 2004; 101(2):540-545.
Monneret, "Histone Deacetylase Inhibitors," *European Journal of Medicinal Chemistry*, 2005; 40:1-13.
Mosmann, T., "Rapid Colorimetric Assay for Cellular Growth and Survival: Application to Proliferation and Cytotoxicity Assays," *Journal of Immunological Methods*, 1983; 65:55-63.
Nawrocki et al., "Aggresome Disruption: A Novel Strategy to Enhance Bortezomib-Induced Apoptosis in Pancreatic Cancer Cells," *Cancer Research*, 2006; 66(7):3773-3781.
Pan P.C. et al., "Soluble Polymer-Supported Synthesis of Arylpiperazines," *Tetrahedron Letters*, 1998; 39:9505-9508.
Patani et al., "Bioisosterism: A Rational Approach in Drug Design," *Chem. Rev.*, 1996; 96: 3147-3176.
Pei Xin-Yan et al., "Synergistic Induction of Oxidative Injury and Apoptosis in Human Multiple Myeloma Cells by the Proteasome Inhibitor Bortezomib and Histone Deacetylase Inhibitors," *Clinical Cancer Research*, 2004; 10:3839-3852.
Simone, J.V., "Oncology: Introduction," *Cecil's Textbook of Medicine*, 1996; 20$^{th}$ Edition, vol. 1:1004-1010.
Sternson et al., "Synthesis of 7200 Small Molecules Based on a Substructural Analysis of the Histone Deacetylase Inhibitors Trichostatin and Trapoxin," *Organic Letters*, 2001; 3(26):4239-4242.
Sutheesophon et al., "Histone Deacetylase Inhibitor Despsipeptides (FK228) Induces Apoptosis in Leukemic Cells by Facilitating Mitochondrial Translocation of Bax, Which is Enhanced by the Proteasome Inhibitor Bortezomib," *ACTA Haematologica*, 2006; 115:78-90.
Takai et al., "Human Ovarian Carcinoma Cells: Histone Deacetylase Inhibitors Exhibit Antiproliferative Activity and Potently Induce Apoptosis," *American Cancer Society*, 2004; 101:2760-2770.
Taylor et al., CAPLUS Abstract 55:33107 (1961).
Van Emelen et al., "Discovery of a Novel Class of Aromatic Hydroxamic Acids as Potent HDAC Inhibitors," *AACR-NCI_Eortc International Conference on Molecular Targets and Cancer Therapeutics*, 2003, XP009095813.
Van Emelen et al., "Synthesis, Biological Evaluation and Structure Activity Relationships of a Novel Servies of Aromatic Hydroxamic Acids as Potent HDAC Inhibitors," *European Journal of Cancer Supp.*, 2004; 2(8):40-41[Poster Session 125].
Walsh et al., "Synthesis and Antiallergy Activity of N-[2-(Dimethylamino)ethyl]-4-aryl-1-piperazinecarboxamide Derivatives," *J. Med. Chemistry*, 1990; 33:2028-2032.
Wolff, Burger's Medicinal Chemistry, 5th Ed. Part 1, pp. 975-977 (1995).
Yokoyama et al., CAPLUS Abstract 105:226622 (1986).
Yokoyama et al., CAPLUS Abstract 105:208919 (1986).
Yu et al., "The Proteasome Inhibitor Bortezomib Interacts Synergistically with Histone Deacetylase Inhibitors to Induce Apoptosis in Bcr/Abl$^+$ Cells Sensitive and Resistant to STI571," *Blood*, 2003; 102:3765-3774.
Cecil's Textbook of Medicine, 1996; 1004-1010.
International Search Report from PCT/EP03/02510 dated May 22, 2003, 2 pages.
International Search Report from PCT/EP03/02511 dated May 22, 2003, 2 pages.
International Search Report from PCT/EP03/02512 dated Jun. 30, 2003, 4 pages.
International Search Report from PCT/EP03/02513 dated May 22, 2003, 2 pages.
International Search Report from PCT/EP03/02514 dated Aug. 13, 2003, 4 pages.
International Search Report from PCT/EP03/02515 dated Aug. 18, 2003, 5 pages.
International Search Report from PCT/EP03/02517 dated May 22, 2003, 2 pages.
International Search Report from PCT/EP05/53611 dated Jan. 17, 2006, 4 pages.
International Search Report from PCT/EP06/62324 dated Aug. 16, 2006, 4 pages.
International Search Report from PCT/EP06/63351 dated Aug. 11, 2006, 2 pages.
International Search Report from PCT/EP06/67656 dated Feb. 6, 2007, 4 pages.
International Search Report from PCT/EP07/50370 dated Mar. 14, 2007, 3 pages.
International Search Report from PCT/EP07/50371 dated May 8, 2007, 4 pages.
International Search Report from PCT/EP07/50374 dated Mar. 12, 2007, 4 pages.
International Search Report from PCT/EP07/50376 dated Mar. 28, 2007, 2 pages.
International Search Report from PCT/EP07/50379 dated May 8, 2007, 3 pages.
International Search Report from PCT/EP07/50381 dated Apr. 4, 2007, 2 pages.
International Search Report from PCT/EP07/59523 dated Mar. 20, 2008, 6 pages.
International Search Report from PCT/EP03/02516 dated Aug. 13, 2003, 3 pages.
International Search Report from PCT/EP05/53612 dated Jul. 10, 2005, 3 pages.
Awada et al., "The pipeline of new anticancer agents for breast cancer treatment in 2003," *Oncology Hematology*, 2003: 48:45-63.
Chemotherapy of Cancer, 1981; 2nd edition; 362-365.
Pasternak et al., "Potent, orally bioavailable somoatostatin agonists; good absorption achieved by urea backbone cyclization," *Bioorganic and Medicinal Chemistry Letters 9*, 1999; 9:491-496.
Calabresi P. and Chabner BA, "Section IX Chemotherapy of Neoplastic Diseases—Introduction," Goodmans & Gilman's *The Pharmacological Basis of Therapeutics*, 10th ed., 2001, Hardman JG, Limbird LE, and Gilman AG, Eds, McGraw-Hill, New York 2001, 1381-1388.
George et al., "A Combination of Histone Deacetylase Inhibitor LBH589 and the Hsp90 Inhibitor 17-AAG is Highly Active Against Human CML-BC Cells and AML Cells with Activating Mutation of FLT-3," *Blood*, 2005; 105(4):1768-1776.

* cited by examiner

SUBSTITUTED AMINOPROPENYL PIPERIDINE OR MORPHOLINE DERIVATIVES AS NOVEL INHIBITORS OF HISTONE DEACETYLASE

CROSS REFERENCE TO RELATED APPLICATIONS

This application is the national stage of PCT Application No. PCT/EP2006/062324, filed 16 May 2006, which claims priority from European Patent Application No. 05104155.6, filed 18 May 2005, the entire disclosures of which are hereby incorporated in their entirely.

This invention concerns compounds having histone deacetylase (HDAC) inhibiting enzymatic activity. It further relates to processes for their preparation, to compositions comprising them, as well as their use, both in vitro and in vivo, to inhibit HDAC and as a medicine, for instance as a medicine to inhibit proliferative conditions, such as cancer and psoriasis.

Nuclear histones are known as integral and dynamic components of the machinery responsible for regulating gene transcription and other DNA-templated processes such as replication, repair, recombination, and chromosome segregation. They are the subject of post-translational modifications including acetylation, phosphorylation, methylation, ubiquitination, and ADP-ribosylation, Histone deacetylase(s), herein referred to as "HDACs", are enzymes that catalyze the removal of the acetyl modification on lysine residues of proteins, including the core nucleosomal histones H2A, H2B, H3 and H4. Together with histone acetyl-transferase(s), herein referred to as "HATs", HDACs regulate the level of acetylation of the histones. The balance of acetylation of nucleosomal histones plays an important role in transcription of many genes. Hypoacetylation of histones is associated with condensed chromatin structure resulting in the repression of gene transcription, whereas acetylated histones are associated with a more open chromatin structure and activation of transcription.

Eleven structurally related HDACs have been described and fall into two classes. Class I HDACs consist of HDAC 1, 2, 3, 8 and 11 whereas class II HDACs consist of HDAC 4, 5, 6, 7, 9 and 10. Members of a third class of HDACs we structurally unrelated to the class I and class II HDACs. Class I/II HDACs operate by zinc-dependent mechanisms, whereas class III HDACs are NAD-dependent.

In addition to histones, other proteins have also been the substrate for acetylation, in particular transcription factors such as p53, GATA-1 and E2F; nuclear receptors such as the glucocorticoid receptor, the thyroid receptors, the estrogen receptors; and cell-cycle regulating proteins such as pRb. Acetylation of proteins has been linked with protein stabilization, such as p53 stabilization, recruitment of cofactors and increased DNA binding. p53 is a tumour suppressor that can induce cell cycle arrest or apoptosis in response to a variety of stress signals, such as DNA damage. The main target for p53-induced cell cycle arrest seems to be the p21 gene. Next to its activation by p53, p21 has been identified by virtue of its association with cyclin/cyclin-dependent kinase complexes resulting in cell cycle arrest at both G1 and G2 phases, its up-regulation during senescence, and its interaction with the proliferating cell nuclear antigen.

The study of inhibitors of HDACs indicates that they play an important role in cell cycle arrest, cellular differentiation, apoptosis and reversal of transformed phenotypes.

The inhibitor Trichostatin A (TSA), for example, causes cell cycle arrest at both G1 and G2 phases, reverts the transformed phenotype of different cell lines, and induces differentiation of Friend leukemia cells and others. TSA (and suberoylanilide hydroxamic acid SAHA) have been reported to inhibit cell growth, induce terminal differentiation, and prevent the formation of tumours in mice (Finnin et al., Nature, 401: 188-193, 1999).

Trichostatin A has also been reported to be useful in the treatment of fibrosis, e.g. liver fibrosis and liver chirrhosis. (Geerts et al., European Patent Application EP 0 827 742, published 11 Mar., 1998).

The pharmacophore for HDAC inhibitors consists of a metal-binding domain, which interacts with the zinc-containing active site of HDACs, a linker domain, and a surface recognition domain or capping region, which interacts with residues on the rim of the active site.

Inhibitors of HDACs have also been reported to induce p21 gene expression. The transcriptional activation of the p21 gene by these inhibitors is promoted by chromatin remodeling, following acetylation of histones H3 and H4 in the p21 promotor region. This activation of p21 occurs in a p53-independent fashion and thus HDAC inhibitors are operative in cells with mutated p53 genes, a hallmark of numerous tumours.

In addition HDAC inhibitors can have indirect activities such as augmentation of the host immune respons and inhibiton of tumor angiogenesis and thus can suppress the growth of primary tumors and impede metastasis (Mai et al., Medicinal Research Reviews, 25: 261-309, 2005).

In view of the above, HDAC inhibitors can have great potential in the treatment of cell proliferative diseases or conditions, including tumours with mutated p53 genes.

Patent application EP1472216 published on Aug. 14, 2003 discloses bicyclic hydroxamates as inhibitors of histone deacetylase.

Patent applications EP1485099, EP1485348, EP1485353, EP1485354, EP1485364, EP1485365, EP1485370, EP1485378 published on 18 Sep., 2003, amongst others, disclose substituted piperazinylpyrimidinylhydroxamic acids as inhibitors of histone deacetylase, furthermore EP1485365 discloses R306465.

Patent application EP1492534 published on 9 Oct., 2003, discloses carbamic acid compounds comprising a piperazine linkage, as HDAC inhibitors.

Patent application EP1495002 published on 23 Oct., 2003, disclose substituted piperazinyl phenyl benzamide compounds, as histone deacetylase inhibitors.

Patent application WO03/092686 published on 13 Nov., 2003, discloses benzamides as histone deacetylase inhibitors.

Patent application WO04/009536 published on 29 Jan., 2004, discloses derivatives containing an alkyl linker between the aryl group and the hydroxamate, as histone deacetylase inhibitors.

Patent application EP1525199 published on 12 Feb., 2004, discloses (hetero)arylalkenyl substituted bicyclic hydroxamates, as histone deacetylase inhibitors.

Patent application EP1572626 published on 24 Jun. 2004, discloses arylene-carboxylic acid (2-amino-phenyl)-amide derivatives as pharmacological agents.

Patent application EP 1581484 published on 29 Jul. 2004, discloses derivatives of N-hydroxy-benzamide derivatives with anti-inflammatory and antitumour activity.

Patent application EP1585735 published on 29 Jul. 2004, discloses substituted aryl hydroxamate derivatives as histone deacetylase inhibitors.

Patent application EP1592667 published on 19 Aug. 2004, discloses mono-acylated O-phenylendiamines derivatives as pharmacological agents.

Patent application EP1590340 published on 19 Aug. 2004, discloses diaminophenylene derivatives as histone deacetylase inhibitors.

Patent application EP 1592665 published on 26 Aug. 2004, discloses benzamide derivatives as histone deacetylase inhibitors.

Patent application WO04/072047 published on 26 Aug. 2004, discloses indoles, benzimidazoles and napbhimidazoles as histone deacetylase inhibitors.

Patent application EP1608628 published on 30 Sep. 2004, discloses hydroxamates linked to non-aromatic heterocyclic ring systems as histone deacetylase inhibitors.

Patent application EP1613622 published on 14 Oct. 2004, discloses oxime derivatives as histone deacetylase inhibitors.

Patent application EP1611088 published on 28 Oct. 2004, discloses hydroxamate derivatives as histone deacetylase inhibitors.

Patent application WO05/028447 published on 31 Mar. 2005, discloses benzimidazoles as histone deacetylase inhibitors.

Patent applications WO05/030704 and WO05/030705 published on 7 Apr. 2005, discloses benzamides as histone deacetylase inhibitors.

Patent application WO05/040101 published on 6 May 2005, discloses acylurea connected and sulfonylurea connected hydroxamates as histone deacetylase inhibitors.

Patent application WO05/040161 also published on 6 May 2005, discloses biaryl linked hydroxamates as histone deacetylase inhibitors.

Patent application WO05/075469 published on 18 Aug. 2005, discloses thiazolyl hydroxamic acids and Thiadiazolyl hydroxamic acids as histone deacetylase inhibitors.

Patent application WO05/086898 published on 22 Sep. 2005, discloses heteropentacyclic hydroxamic acids as histone deacetylase inhibitors.

Patent application WO05/092899 published on 6 Oct. 2005, discloses alkenylbenzamides as histone deacetylases.

The compounds of the present invention differ from the prior art in structure, in their pharmacological activity and/or pharmacological potency.

The problem to be solved is to provide histone deacetylase inhibitors with high enzymatic and cellular activity that have increased bioavailability and/or in vivo potency.

The novel compounds of the present invention solve the above-described problem. The compounds of the present invention show excellent histone deacetylase inhibiting enzymatic and cellular activity. They have a high capacity to activate the p21 gene, both at the cellular and the in vivo level. They have a desirable pharmacokinetic profile and can have low affinity for the P450 enzymes, which reduces the risk of adverse drug-drug interaction allowing also for a wider safety margin.

Advantageous features of the present compounds are metabolic stability, solubility and/or p21 induction capacity. More in particular the compounds of the present invention have increased half-lives in rat hepatocytes, have an increased solubility/stability in aqueous solutions and/or have enhanced in vivo p21 promotor inducing capacities.

This invention concerns compounds of formula (I)

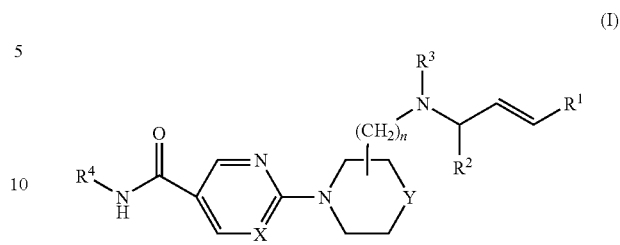

(I)

the N-oxide forms, the pharmaceutically acceptable addition salts and the stereo-chemically isomeric forms thereof, wherein each X is independently N or CH;

each Y is independently O, CH or $CH_2$ and when Y is CH then the substituent is attached to the Y atom of the ring structure;

n is 0 or 1 and when n is 0 than a direct bond is intended;

$R^1$ is phenyl, naphtalenyl or heterocyclyl; wherein
  each of said phenyl or naphtalenyl is optionally substituted with one or two substituents each independently selected from halo, $C_{1-6}$alkyl, $C_{1-6}$alkyloxy, polyhalo$C_{1-6}$alkyl, aryl, hydroxy, cyano, amino, $C_{1-6}$alkylcarbonylamino, $C_{1-6}$alkylsulfonylamino, hydroxycarbonyl, $C_{1-6}$alkyloxycarbonyl, hydroxy$C_{1-6}$alkyl, $C_{1-6}$alkyloxymethyl, aminomethyl, $C_{1-6}$alkylaminomethyl, $C_{1-6}$alkylcarbonylaminomethyl, $C_{1-6}$alkylsulfonylaminomethyl, aminosulfonyl, $C_{1-6}$alkylaminosulfonyl or heterocyclyl;

$R^2$ is —$CH_2$—$R^5$, trifluoromethyl, —C(=O)—$R^6$, or —$CH_2$—$NR^7R^8$; wherein
  each $R^5$ is independently selected from hydrogen, hydroxy, $C_{1-6}$alkyloxy, piperazinyl, N-methylpiperazinyl, morpholinyl, thiomorpholinyl, imidazolyl or triazolyl;
  each $R^6$ is independently selected from hydroxy, $C_{1-6}$alkyloxy, amino or mono- or di($C_{1-6}$alkyl)amino, $C_{3-6}$cycloalkylamino, piperazinyl, N-methylpiperazinyl, morpholinyl or thiomorpholinyl;
  each $R^7$ and $R^8$ are independently selected from hydrogen, $C_{1-6}$alkyl, $C_{1-6}$alkylcarbonyl, $C_{1-6}$alkylsulfonyl, or mono- or di($C_{1-4}$alkyl)aminosulfonyl;

$R^3$ is hydrogen, $C_{1-6}$alkyl, cyano$C_{1-4}$alkyl, $C_{1-6}$alkyloxycarbonyl, hydroxy$C_{1-6}$alkyl, $C_{1-6}$alkyloxy$C_{1-6}$alkyl, $C_{3-6}$cycloalkyl, $C_{3-6}$cycloalkyl$C_{1-6}$alkyl, aryl$C_{1-6}$alkyl, $C_{1-6}$alkylcarbonyl, $C_{1-6}$alkylsulfonyl;

$R^4$ is hydroxy or a radical of formula (a-1)

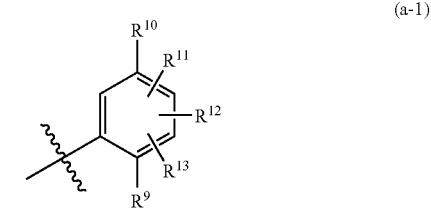

(a-1)

wherein
  $R^9$ is hydroxy or —$NH_2$;
  $R^{10}$ is hydrogen, thienyl, furanyl or phenyl and each thienyl, furanyl or phenyl can optionally be substituted with halo, amino, nitro, cyano, hydroxy, phenyl, $C_{1-6}$alkyl, (di$C_{1-6}$alkyl)amino, $C_{1-6}$alkyloxy, phenyl$C_{1-6}$alkyloxy, hydroxy$C_{1-6}$alkyl, $C_{1-6}$alkyloxycarbonyl, hydroxycarbonyl, $C_{1-6}$alkylcarbonyl, polyhalo$C_{1-6}$alkyloxy, polyhaloC$_{1-6}$alkyl, C$_{1-6}$alkylsulfonyl, hydroxycarbonylC$_{1-6}$alkyl, C$_{1-6}$alkylcarbonylamino, aminosulfonyl, aminosulfonylC$_{1-6}$alkyl, isoxazolyl, aminocarbonyl, phenylC$_{2-6}$alkenyl, phenylC$_{3-6}$alkynyl or pyridinylC$_{3-6}$alkynyl;

R$^{11}$, R$^{12}$ and R$^{13}$ are each independently hydrogen, —NH$_2$, nitro, furanyl, halo, C$_{1-6}$alkyl, C$_{1-6}$alkyloxy, trifluoromethyl, thienyl, phenyl, C$_{1-6}$alkylcarbonylamino, aminocarbonylC$_{1-6}$alkyl or —C≡C—CH$_2$—R$^{14}$;

wherein R$^{14}$ is hydrogen, C$_{1-6}$alkyl, hydroxy, amino or C$_{1-6}$alkyloxy; and heterocyclyl in the above is furanyl, thienyl, pyrrolyl, pyrrolinyl, pyrrolidinyl, dioxolyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, dithianyl, thiomorpholinyl, pyridazinyl, pyrimidinyl, pyrazinyl, piperazinyl, triazinyl, trithianyl, indolizinyl, indolyl, indolinyl, benzofuranyl, benzothiophenyl, indazolyl, benzimidazolyl, benzthiazolyl, purinyl, quinolizinyl, quinolinyl, cinnolinyl, phthlazinyl, quinazolinyl, quinoxalinyl or naphthyridinyl; wherein each of said heterocycles is optionally substituted with one or two substituents each independently selected from halo, C$_{1-6}$alkyl, C$_{1-6}$alkyloxy, cyano, amino, mono- or di(C$_{1-4}$alkyl)amino.

Lines drawn into ring systems from substituents indicate that the bond may be attached to any of the suitable ring atoms of the ring system.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone. Preferably, such inhibition is specific, i.e. the histone deacetylase inhibitor reduces the ability of a histone deacetylase to remove an acetyl group from a histone at a concentration that is lower than the concentration of the inhibitor that is required to produce some other, unrelated biological effect.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; C$_{1-6}$alkyl includes C$_{1-4}$alkyl and the higher homologues thereof having 5 to 6 carbon atoms such as, for example, pentyl, 2-methyl-butyl, hexyl, 2-methylpentyl and the like; polyhaloC$_{1-6}$alkyl defines C$_{1-6}$alkyl containing three identical or different halo substituents for example trifluoromethyl; C$_{3-6}$cycloalkyl includes cyclic hydrocarbon groups having from 3 to 6 carbons, such as cyclopropyl, cyclobutyl, cyclopentyl, cyclopentenyl, cyclohexyl and the like and aryl is phenyl, or phenyl substituted with one or more substituents each independently selected from halo, C$_{1-6}$alkyl, C$_{1-6}$alkyloxy, trifluoromethyl, cyano or hydroxycarbonyl.

Pharmaceutically acceptable addition salts encompass pharmaceutically acceptable acid addition salts and pharmaceutically acceptable base addition salts. The pharmaceutically acceptable acid addition salts as mentioned hereinabove are meant to comprise the therapeutically active non-toxic acid addition salt forms, which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, trifluoroacetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "acid or base addition salts" also comprises the hydrates and the solvent addition forms, which the compounds of formula (I) are able to form. Examples of such forms are e.g. hydrates, alcoholates and the like.

The term "stereochemically isomeric forms of compounds of formula (I)", as used herein, defines all possible compounds made up of the same atoms bonded by the same sequence of bonds but having different three-dimensional structures, which are not interchangeable, which the compounds of formula (I) may possess. Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

The N-oxide forms of the compounds of formula (I) are meant to comprise those compounds of formula (I) wherein one or several nitrogen atoms are oxidized to the so-called N-oxide, particularly those N-oxides wherein one or more of the piperidine-, piperazine or pyridazinyl-nitrogens are N-oxidized.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable addition salts and all stereoisomeric forms.

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9, HDAC-10 and HDAC-11. The histone deacetylase can also be derived from a protozoal or fungal source.

A first group of interesting compounds consists of those compounds of formula (I) wherein one or more of the following restrictions apply:
a) each X is N;
b) each Y is independently O or CH;
c) R$^1$ is phenyl or phenyl optionally substituted with C$_{1-6}$alkyloxy, polyhaloC$_{1-6}$alkyl, aryl or halo, more in particular phenyl substituted with 4-fluoro;
d) R$^2$ is —CH$_2$—R$^5$ or —C(=O)—R$^6$;

e) each $R^5$ is independently selected from hydrogen, hydroxy, $C_{1-6}$alkyloxy, $C_{1-6}$alkyloxy$C_{1-6}$alkyloxy, $C_{1-6}$alkylcarbonyloxy, N-methylpiperazinyl, morpholinyl, or imidazolyl;
f) each $R^6$ is independently selected from $C_{1-6}$alkylamino, $C_{1-6}$cycloalkylamino, hydroxy$C_{1-6}$alkylamino, di($C_{1-6}$alkyl)amino$C_{1-6}$alkylamino or morpholinyl;
g) $R^3$ is hydrogen, $C_{1-6}$alkylcarbonyl or $C_{1-6}$alkylsulfonyl.
h) $R^9$ is —$NH_2$;
i) $R^{10}$ is hydrogen; or
j) $R^{11}$, $R^{12}$ and $R^{13}$ are each independently hydrogen.

A second group of interesting compounds consists of those compounds of formula (I) wherein one or more of the following restrictions apply:
a) each X is N;
b) each Y is independently O or CH;
c) $R^1$ is phenyl;
d) $R^2$ is —$CH_2OH$ or methyl;
e) $R^3$ is hydrogen, $C_{1-6}$alkylcarbonyl or $C_{1-6}$alkylsulfonyl;
f) $R^9$ is —$NH_2$;
g) $R^{10}$ is hydrogen; or
h) $R^{11}$, $R^{12}$ and $R^{13}$ are each independently hydrogen.

A third group of interesting compounds consists of those compounds of formula (I) wherein one or more of the following restrictions apply.
a) each X is N;
b) each Y is CH;
c) n is 1;
d) $R^1$ is phenyl;
e) $R^2$ is —$CH_2$—$R^5$ or methyl;
f) each $R^5$ is independently selected from hydrogen, hydroxy, $C_{1-6}$alkyloxy, or $C_{1-6}$alkylcarbonyloxy;
g) $R^3$ is hydrogen or $C_{1-6}$alkylsulfonyl; or
h) $R^4$ is hydroxy.

A fourth group of interesting compounds consists of those compounds of formula (I) wherein one or more of the following restrictions apply:
a) each X is N;
b) each Y is CH;
c) n is 1;
d) $R^1$ is phenyl;
e) $R^2$ is —$CH_2OH$ or methyl;
f) $R^3$ is hydrogen or $C_{1-6}$alkylsulfonyl; or
g) $R^4$ is hydroxy.

A group of preferred compounds consists of those compounds of formula (I) wherein each X is N; each Y is independently O or CH; $R^1$ is phenyl; $R^2$ is —$CH_2OH$ or methyl; $R^3$ is hydrogen, $C_{1-6}$alkylcarbonyl or $C_{1-6}$alkylsulfonyl; $R^9$ is —$NH_2$; $R^{10}$ is hydrogen; and $R^{11}$, $R^{12}$ and $R^{13}$ are each independently hydrogen.

A group of more preferred compounds consists of those compounds of formula (I) wherein each X is N; each Y is CH; n is 1; $R^1$ is phenyl; $R^2$ is —$CH_2OH$ or methyl; $R^3$ is hydrogen or $C_{1-6}$alkylsulfonyl; and $R^4$ is hydroxy.

The most preferred compounds are compound No. 1. and compound No. 8.

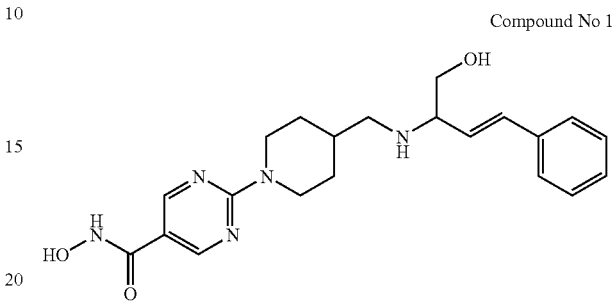

Compound No 1

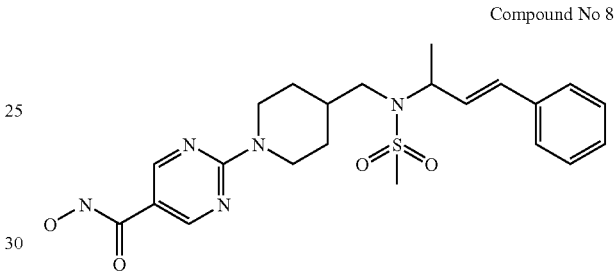

Compound No 8

The compounds of formula (I) and their pharmaceutically acceptable salts and N-oxides and stereochemically isomeric forms thereof may be prepared in conventional manner. The starting materials and some of the intermediates are known compounds and are commercially available or may be prepared according to conventional reaction procedures generally known in the art.

Some preparation methods will be described hereinafter in more detail. Other methods for obtaining final compounds of formula (I) are described in the examples.

Compounds of formula (I), wherein $R^4$ is hydroxy, herein referred to as compounds of formula (I-a) can be prepared by reacting an intermediate of formula (II) with an appropriate acid, such as for example, trifluoro acetic acid. Said reaction is performed in an appropriate solvent, such as, for example, methanol or dichloromethane.

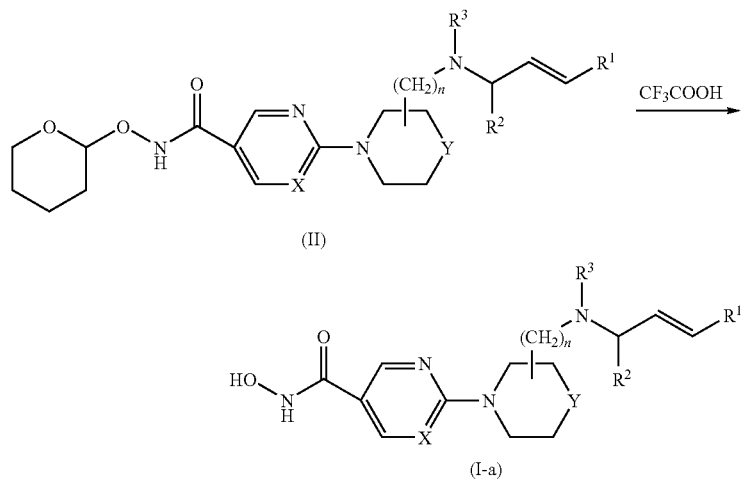

Compounds of formula (I), wherein $R^4$ is a radical of formula (a-1) and $R^9$ is —$NH_2$, herein referred to as compounds of formula (I-b) can be prepared by reacting an intermediate of formula (III) wherein M represents hydrogen, or sodium or lithium or an alkali metal cation: for example sodium, with an intermediate of formula (IV) in the presence of appropriate reagents such as for example benzotriazol-1-yloxytris(pyrrolidino)phosphonium hexafluorophosphate (PyBOP). The reaction may be performed in the presence of a base such as triethylamine, in a suitable solvent, such as, a mixture of dichloromethane and tetrahydrofuran.

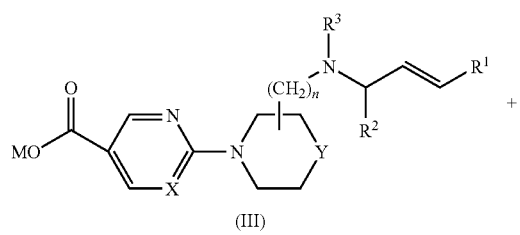

(III)

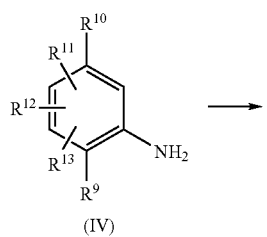

(IV)

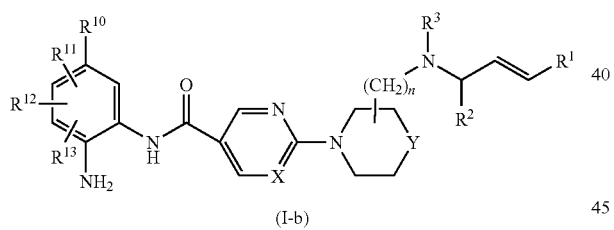

(I-b)

Compounds of formula (I-b) may also be prepared by reacting an intermediate of formula (V) with an appropriate acid, such as for example, trifluoroacetic acid. Said reaction is performed in an appropriate solvent, such as, for example, methanol or dichloromethane.

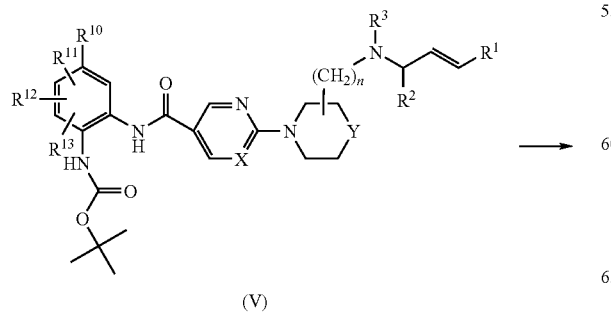

(V)

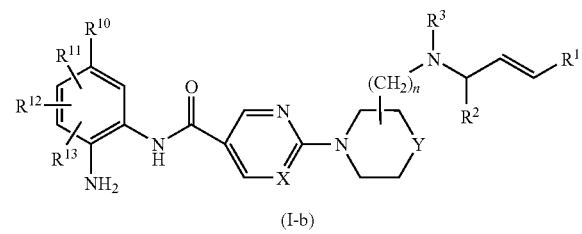

(I-b)

Compounds of formula (I), wherein $R^4$ is a radical of formula (a-1) and $R^9$ is hydroxy, herein referred to as compounds of formula (I-c) may be prepared by reacting an intermediate of formula (VI) with tetrabutylammonium fluoride in an appropriate solvent such as, for example tetrahydrofuran. TBDMS in the intermediate of formula (VI) means tert-butyl (dimethyl)silanyl.

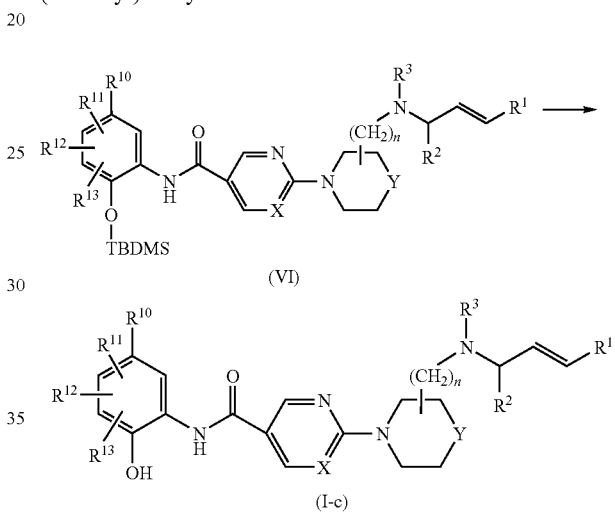

(VI)

(I-c)

Intermediates of formula (II) can be prepared by reacting an intermediate of formula (III) with an intermediate of formula (VII) in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction may be performed in the presence of a base such as triethylamine, in a suitable solvent, such as, a mixture of dichloromethane and tetrahydrofuran.

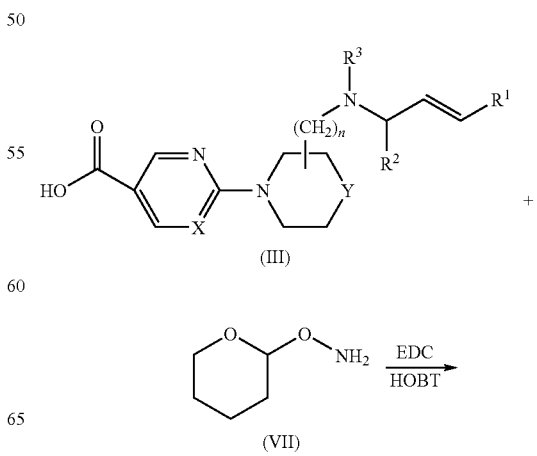

(III)

(VII)

-continued

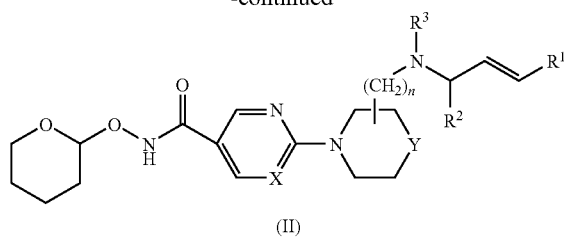

(II)

Intermediates of formula (III) may be prepared by reacting an intermediate of formula (VIII) with an appropriate acidic solution, e.g. hydrochloric acid, or basic solution, e.g. lithiumhydroxide or sodiumhydroxide, in a suitable solvent e.g. an alcohol, such as ethanol or propanol.

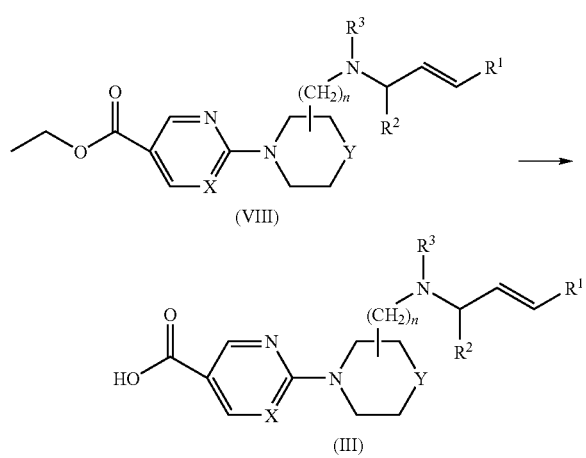

The present invention also concerns compounds of formula (VIII)

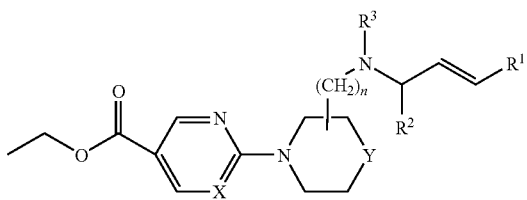

(VIII)

the N-oxide forms, the pharmaceutically acceptable addition salts and the stereo-chemically isomeric forms thereof, wherein each X is independently N or CH;
each Y is independently O, CH or $CH_2$ and when Y is CH then the substituent is attached to the Y atom of the ring structure;
n is 0 or 1 and when n is 0 than a direct bond is intended;
$R^1$ is phenyl, naphtalenyl or heterocyclyl; wherein
each of said phenyl or naphtalenyl is optionally substituted with one or two substituents each independently selected from halo, $C_{1-6}$alkyl, $C_{1-6}$alkyloxy, polyhalo$C_{1-6}$alkyl, aryl, hydroxy, cyano, amino, 9$C_{1-6}$alkylcarbonylamino, $C_{1-6}$alkyl sulfonylamino, hydroxycarbonyl, $C_{1-6}$alkyloxycarbonyl, hydroxy$C_{1-6}$alkyl, $C_{1-6}$alkyloxymethyl, aminomethyl, $C_{1-6}$alkylaminomethyl, $C_{1-6}$alkylcarbonylaminomethyl, $C_{1-6}$alkylsulfonylaminomethyl, amino sulfonyl, $C_{1-6}$alkylaminosulfonyl or heterocyclyl;

$R^2$ is —$CH_1$—$R^4$, trifluoromethyl, —C(═O)—$R^5$, or —$CH_2$—$NR^6R^7$; wherein
each $R^4$ is independently selected from hydrogen, hydroxy, $C_{1-6}$alkyloxy, piperazinyl, N-methylpiperazinyl, morpholinyl, thiomorpholinyl, imidazolyl or triazolyl; each $R^5$ is independently selected from hydroxy, $C_{1-6}$alkyloxy, amino or mono- or di ($C_{1-6}$alkyl)amino, $C_{1-6}$cycloalkylamino, piperazinyl, N-methylpiperazinyl, morpholinyl or thiomorpholinyl;

each $R^6$ and $R^7$ are independently selected from hydrogen, $C_{1-6}$alkyl, $C_{1-6}$alkylcarbonyl, $C_{1-6}$alkylsulfonyl, or mono- or di($C_{1-4}$alkyl)aminosulfonyl;

$R^3$ is hydrogen, $C_{1-6}$alkyl, cyano$C_{1-4}$alkyl, $C_{1-6}$alkyloxycarbonyl, hydroxy$C_{1-6}$alkyl, $C_{1-6}$alkyloxy$C_{1-6}$alkyl, $C_{3-6}$cycloalkyl, $C_{3-6}$cycloalkyl$C_{1-6}$alkyl, aryl$C_{1-6}$alkyl, $C_{1-6}$alkylcarbonyl, $C_{1-6}$alkylsulfonyl; and heterocyclyl in the above is furanyl, thienyl, pyrrolyl, pyrrolinyl, pyrrolidinyl, dioxolyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridinyl, piperidinyl, dioxanyl, morpholinyl, dithianyl, thiomorpholinyl, pyridazinyl, pyrimidinyl, pyrazinyl, piperazinyl, triazinyl, trithianyl, indolizinyl, indolyl, indolinyl, benzofuranyl, benzothiophenyl, indazolyl, benzimidazolyl, benzthiazolyl, purinyl, quinolizinyl, quinolinyl, cinnolinyl, phthlazinyl, quinazolinyl, quinazolinyl or naphthyridinyl; wherein each of said heterocycles is optionally substituted with one or two substituents each independently selected from halo, $C_{1-6}$alkyl, $C_{1-6}$alkyloxy, cyano, amino, or mono- or di($C_{1-4}$alkyl)amino.

Groups of interesting, preferred, more preferred and most preferred compounds can be defined for the compounds of formula (V), in accordance with the groups defined for the compounds of formula (I).

The novel intermediates of formula (VIII) can be prepared by:

Converting intermediates of formula (VIII), wherein $R^2$ is —$CH_2OH$, herein referred to as intermediates of formula (VIII-a), into intermediates of formula (VIII) wherein $R^2$ is other than —$CH_2OH$, herein referred to as intermediates of formula (VIII-b), via art-known reactions or functional group transformations. For example the alcohols of formula (VIII-a) can be converted into amines, esters and ethers. The primary amines can be converted to secondary or tertiary amines, and/or primary or secondary amines can be converted into amides.

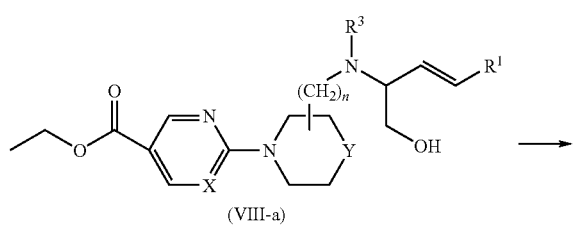

(VIII-a)

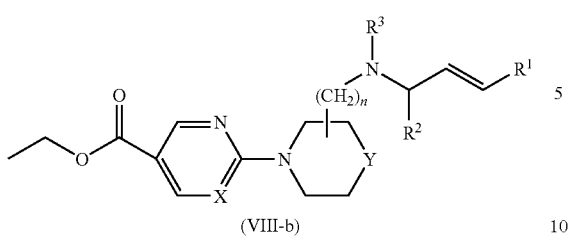

(VIII-b)

The novel intermediates of formula (VIII), wherein $R^2$ is —$CH_2OH$ and $R^3$ is hydrogen, herein referred to as intermediates of formula (VIII-c) can be prepared in a single step by reacting the intermediate of formula (IX), with 1,4-dioxane-2,5-diol and the appropriate boronic acid of formula (X), wherein $R^1$ is as defined above, in a suitable solvent, e.g. an alcohol, such as ethanol.

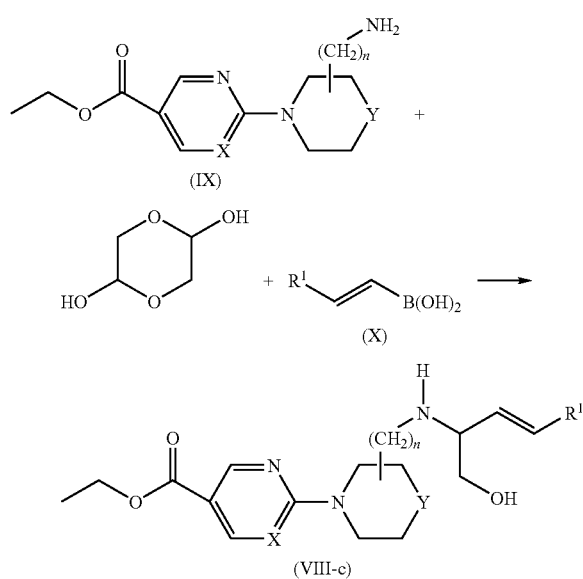

(VIII-c)

The novel intermediates of formula (VIII), wherein $R^2$ is other than —$CH_2OH$ and $R^3$ is hydrogen, herein referred to as intermediates of formula (VIII-d), can be prepared by reacting the intermediates of formula (IX) with the appropriate ketone of formula (XI) in the presence of an appropriate reagent, such as tetrakis(ethanolato)titanium or a sodium borohydride, in a suitable solvent e.g. 1,2-dichloroethane.

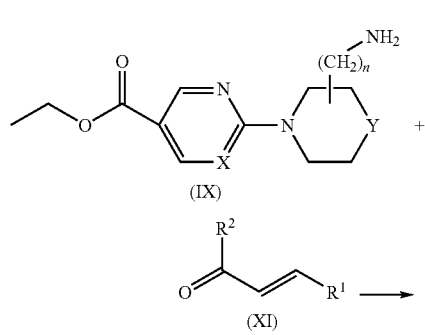

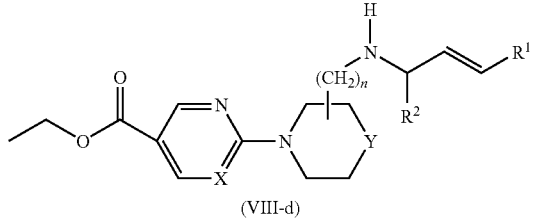

(VIII-d)

Intermediates of formula (IX), wherein Y is O, herein referred to as intermediates of (IX-a), can be prepared by reacting an intermediate of formula (XII) with an appropriate acid, such as for example, trifluoro acetic acid. Said reaction is performed in an appropriate solvent, such as, for example, methanol or dichloromethane.

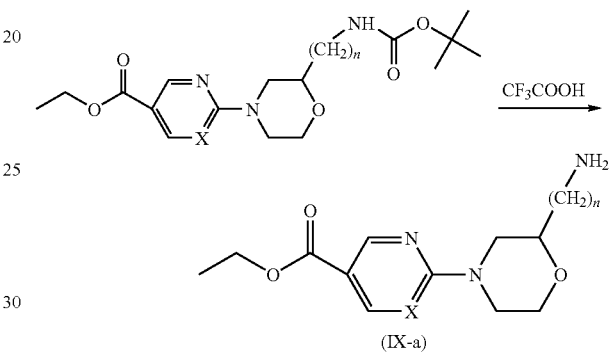

(IX-a)

Intermediates of formula (XII) can be prepared by reacting an intermediate of formula (XIII) with an intermediate of formula (XIV) wherein W is an appropriate leaving group such as, for example, halo, e.g. chloro or a sulfonyl radical such as methylsulfonyl and the like. The reaction can be performed in a reaction-inert solvent such as, for example, N,N-dimethylformamide, nitrobenzene, acetonitrile and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

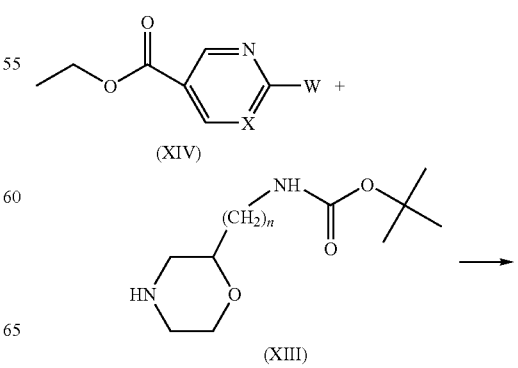

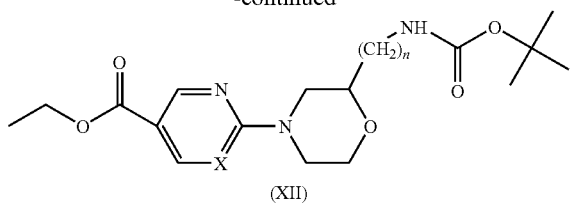

(XII)

In an identical way, the intermediates of formula (VIII) can be prepared by reacting an intermediate of formula (VIII-d) with an intermediate of formula (XV) wherein W is an appropriate leaving group as defined above

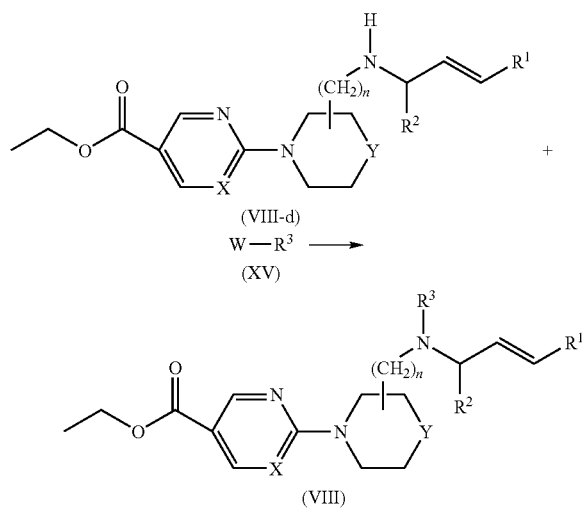

The compounds of formula (I) and some of the intermediates may have at least one stereogenic centre in their structure. This stereogenic centre may be present in an R or an S configuration.

The compounds of formula (I) as prepared in the hereinabove described processes are generally racemic mixtures of enantiomers, which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) or of the intermediates of formula (V-b), involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they have a histone deacetylase (HDAC) inhibitory effect.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a compound of the present invention, to a subject, e.g. a mammal (and more particularly a human) in need of such treatment. In particular, this invention provides a method for inhibiting the growth of tumours by the administration of an effective amount of the compounds of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The compound according to the invention may be used for other therapeutic purposes, for example:
a) the sensitisation of tumours to radiotherapy by administering the compound according to the invention before, during or after irradiation of the tumour for treating cancer;
b) treating arthropathies and osteopathological conditions such as rheumatoid arthritis, osteoarthritis, juvenile arthritis, gout, polyarthritis, psoriatic arthritis, ankylosing spondylitis and systemic lupus erythematosus;
c) inhibiting smooth muscle cell proliferation including vascular proliferative disorders, atherosclerosis and restenosis;
d) treating inflammatory conditions and dermal conditions such as ulcerative colitis, Crohn's disease, allergic rhinitis, graft vs. host disease, conjunctivitis, asthma, ARDS, Behcets disease, transplant rejection, uticaria, allergic dermatitis, alopecia areata, scleroderma, exanthema, eczema, dermatomyositis, acne, diabetes, systemic lupus erythematosis, Kawasaki's disease, multiple sclerosis, emphysema, cystic fibrosis and chronic bronchitis;
e) treating endometriosis, uterine fibroids, dysfunctional uterine bleeding and endometrial hyperplasia;
f) treating ocular vascularisation including vasculopathy affecting retinal and choroidal vessels;
g) treating a cardiac dysfunction;
h) inhibiting immunosuppressive conditions such as the treatment of HIV infections;
i) treating renal dysfunction;
j) suppressing endocrine disorders;
k) inhibiting dysfunction of gluconeogenesis;
l) treating a neuropathology for example Parkinson's disease or a neuropathology that results in a cognitive disorder, for example, Alzheimer's disease or polyglutamine related neuronal diseases;

m) treating psychiatric disorders for example schizophrenia, bipolar disorder, depression, anxiety and psychosis;
n) inhibiting a neuromuscular pathology, for example, amylotrophic lateral sclerosis;
o) treating spinal muscular atrophy;
p) treating other pathologic conditions amenable to treatment by potentiating expression of a gene;
q) enhancing gene therapy;
r) inhibiting adipogenesis;
s) treating parasitosis such as malaria.

Hence, the present invention discloses the compounds of formula (I) for use as a medicine as well as the use of these compounds of formula (I) for the manufacture of a medicament for treating one or more of the above mentioned conditions.

The compounds of formula (I), the pharmaceutically acceptable acid addition salts and stereoisomeric forms thereof can have valuable diagnostic properties in that they can be used for detecting or identifying a HDAC in a biological sample comprising detecting or measuring the formation of a complex between a labelled compound and a HDAC.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 10 mg to 500 mg of active ingredient per unit dosage form.

As another aspect of the present invention a combination of a HDAC-inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents. Examples of anti-cancer agents are:
platinum coordination compounds for example cisplatin, carboplatin or oxalyplatin;
taxane compounds for example paclitaxel or docetaxel;
topoisomerase I inhibitors such as camptothecin compounds for example irinotecan or topotecan;
topoisomerase II inhibitors such as anti-tumour podophyllotoxin derivatives for example etoposide or teniposide;
anti-tumour vinca alkaloids for example vinblastine, vincristine or vinorelbine;
anti-tumour nucleoside derivatives for example 5-fluorouracil, gemcitabine or capecitabine;
alkylating agents such as nitrogen mustard or nitrosourea for example cyclophosphamide, chlorambucil, carmustine or lomustine;
anti-tumour anthracycline derivatives for example daunorubicin, doxorubicin, idarubicin or mitoxantrone;
HER2 antibodies for example trastuzumab;
estrogen receptor antagonists or selective estrogen receptor modulators for example tamoxifen, toremifene, droloxifene, faslodex or raloxifene;
aromatase inhibitors such as exemestane, anastrozole, letrazole and vorozole;
differentiating agents such as retinoids, vitamin D and retinoic acid metabolism blocking agents (RAMBA) for example accutane;
DNA methyl transferase inhibitors for example azacytidine;

kinase inhibitors for example flavoperidol, imatinib mesylate or gefitinib;
farnesyltransferase inhibitors;
other HDAC inhibitors;
inhibitors of the ubiquitin-proteasome pathway for example Velcade; or
Yondelis.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree *Camptothecin acuminata* and the Indian tree *Nothapodytes foetida*.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (*Vinca rosea*).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus *Strep. peuticus* var. caesius and their derivatives, characterised by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis)

The term "farnesyltransferase inhibitors" is used to indicate compounds that were designed to prevent farnesylation of Ras and other intracellular proteins. They have been shown to have effect on malignant cell proliferation and survival.

The term "other HDAC inhibitors" comprises but is not limited to:
carboxylates for example butyrate, cinnamic acid, 4-phenylbutyrate or valproic acid;
hydroxamic acids for example suberoylanilide hydroxamic acid (SAHA), piperazine containing SAHA analogues, biaryl hydroxamate A-161906 and its carbozolyether-, tetrahydropyridine- and tetralone-analogues, bicyclic aryl-N-hydroxycarboxamides, pyroxamide, CG-1521, PXD-101, sulfonamide hydroxamic acid, LAQ-824, trichostatin A (TSA), oxamflatin, scriptaid, scriptaid related tricyclic molecules, m-carboxy cinnamic acid bishydroxamic acid (CBHA), CBHA-like hydroxamic acids, trapoxin-hydroxamic acid analogue, R306465 and related benzoyl- and heteroaryl-hydroxamic acids, aminosuberates and malonyldiamides;
cyclic tetrapeptides for example trapoxin, apidicin, depsipeptide, spiruchostatin-related compounds, RedFK-228, sulfhydryl-containing cyclic tetrapeptides (SCOPs), hydroxamic acid containing cyclic tetrapeptides (CHAPs), TAN-174s and azumamides;
benzamides for example MS-275 or CI-994, or
depudecin.

The term "inhibitors of the ubiquitin-proteasome pathway" is used to identify compounds that inhibit the targeted destruction of cellular proteins in the proteasome, including cell cycle regulatory proteins.

For the treatment of cancer the compounds according to the present invention may be administered to a patient as described above, in conjunction with irradiation. Irradiation means ionising radiation and in particular gamma radiation, especially that emitted by linear accelerators or by radionuclides that are in common use today. The irradiation of the tumour by radionuclides can be external or internal.

The present invention also relates to a combination of an anti-cancer agent and a HDAC inhibitor according to the invention.

The present invention also relates to a combination according to the invention for use in medical therapy for example for inhibiting the growth of tumour cells.

The present invention also relates to a combinations according to the invention for inhibiting the growth of tumour cells.

The present invention also relates to a method of inhibiting the growth of tumour cells in a human subject which comprises administering to the subject an effective amount of a combination according to the invention.

This invention further provides a method for inhibiting the abnormal growth of cells, including transformed cells, by administering an effective amount of a combination according to the invention.

The other medicinal agent and HDAC inhibitor may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and HDAC inhibitor being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

Trastuzumab is advantageously administered in a dosage of 1 to 5 mg per square meter ($mg/m^2$) of body surface area, particularly 2 to 4 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

These dosages may be administered for example once, twice or more per course of treatment, which may be repeated for example every 7, 14, 21 or 28 days.

In view of their useful pharmacological properties, the components of the combinations according to the invention, i.e. the other medicinal agent and the HDAC inhibitor may be formulated into various pharmaceutical forms for administration purposes. The components may be formulated separately in individual pharmaceutical compositions or in a unitary pharmaceutical composition containing both components.

The present invention therefore also relates to a pharmaceutical composition comprising the other medicinal agent and the HDAC inhibitor together with one or more pharmaceutical carriers.

The present invention also relates to a combination according to the invention in the form of a pharmaceutical composition comprising an anti-cancer agent and a HDAC inhibitor according to the invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a HDAC inhibitor according to the invention and as second active ingredient an anticancer agent, as a combined preparation for simultaneous, separate or sequential use in the treatment of patients suffering from cancer.

EXPERIMENTAL PART

The following examples are provided for purposes of illustration.

Hereinafter, "DCM" is defined as dichloromethane, "DIPE" is defined as diisopropyl ether, "EDC" is defined as N'-(ethylcarbonimidoyl)-N,N-dimethyl-1,3-propanediamine, monohydrochloride, "EtOAc" is defined as ethyl acetate, "EtOH" is defined as ethanol, "HOBT" is defined as 1-hydroxy-1H-benzotriazole, "MeOH" is defined as methanol, "PyBOP" is defined as phosphorus(1+), (1-hydroxy-1H-benzotriazolato-O)tri-1-pyrrolidinyl-, (T-4)-, hexafluorophosphate(1−), "TFA" is defined as trifluoroacetic acid and "THF" is defined as tetrahydrofuran.

A. Preparation of the Intermediate Compounds

Example A1 a) Preparation of intermediate 1

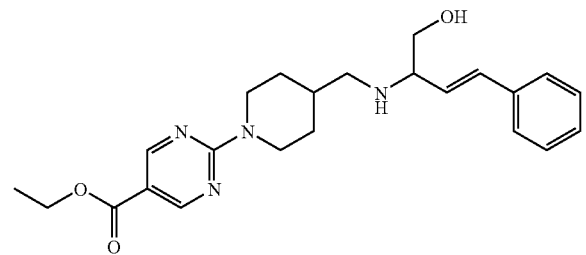

A mixture of 2-(4-aminomethyl-piperidin-1-yl)-pyrimidine-5-carboxylic acid ethyl ester (0.003 mol), (2-phenylethenyl)-boronic acid (0.003 mol) and 1,4-dioxane-2,5-diol (0.003 mol) in EtOH (40 ml) was stirred for 2 days at room temperature and then the solvent was evaporated (vac.), yielding intermediate 1 (used as such in the next reaction step without further purification).

b) Preparation of intermediate 2

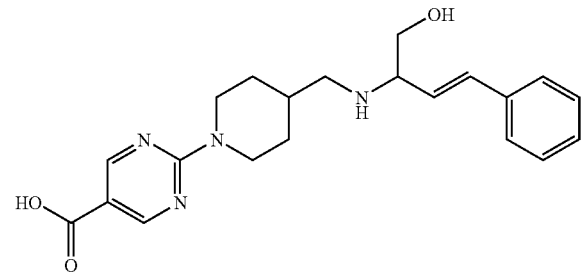

A mixture of intermediate 1 (0.0014 mol) in sodium hydroxide 1N (10 ml) and THF (30 ml) was stirred at room temperature for 48 hours. Hydrochloric acid 1N (10 ml) was added. The solvent was evaporated, yielding intermediate 2 (used as such in the next reaction step without further purification).

c) Preparation of intermediate 3

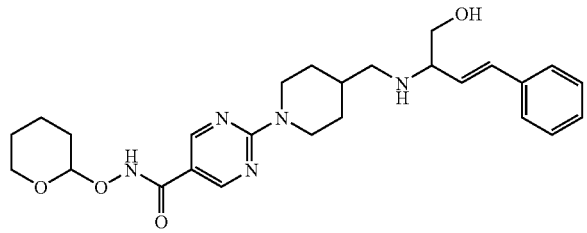

Triethyl amine (0.0042 mol), N'-(ethylcarbonimidoyl)-N,N-dimethyl-1,3-propanediamine (0.0021 mol), 1-hydroxy-1H-benzotriazole (0.0021 mol) and O-(tetrahydro-2H-pyran-2-yl)-hydroxylamine (0.0021 mol) were added to a mixture of intermediate 2 (0.0014 mol) in a mixture of DCM (30 ml) and THF (30 ml), then the reaction mixture was stirred for 5 hours at 40° C. Water was added. The organic layer was separated, dried (MgSO$_4$), filtered off and the solvent was evaporated. The residue was purified by column chromatography (5 μm) (gradient eluent: DCM/MeOH/NH$_4$OH 99/1/0.5 to 95/5/0.25). The product fractions were collected and the organic solvent was evaporated yielding 0.03 g (4%) of intermediate 3.

Example A2 a) Preparation of intermediate 4

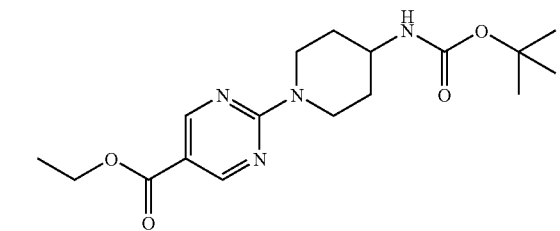

A solution of 2-methanesulfonyl-pyrimidine-5-carboxylic acid ethyl ester (0.0434 mol) in acetonitrile is added under nitrogen to a solution of 4-N-(tertbutoxycarbonyl)aminopiperidine (0.0362 mol) and potassium carbonate (0.0724 mol). The mixture was stirred at room temperature for 15 hours, poured out onto ice. The precipitate was filtered, washed with water and DIPE and dried yielding 7.9 g of intermediate 4.

b) Preparation of intermediate 5

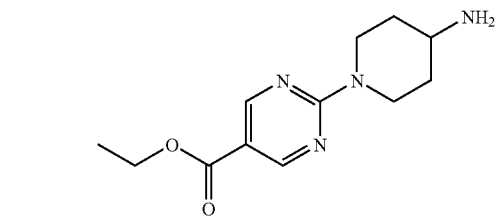

Trifluoro acetic acid (20 ml) was added at room temperature to a solution of intermediate 4 (0.0225 mol) in DCM (110 ml). The mixture was stirred at room temperature for 15 hours, then evaporated till dryness. The residue was taken up in EtOAc. Water was added. K$_2$CO$_3$ was added. EtOAc was evaporated. The precipitate was filtered, washed with water, then with diethyl ether and dried. The mixture was extracted with DCM, the organic layer was separated, dried (MgSO₄), filtered and the solvent was evaporated, yielding 2 g of intermediate 5.

c) Preparation of intermediate 6

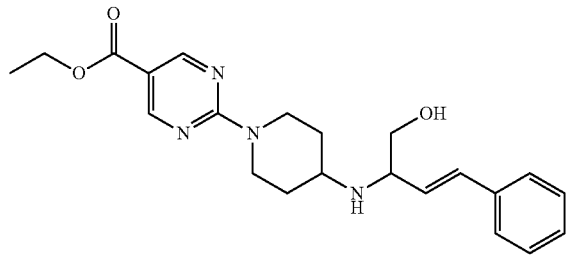

(2-phenylethenyl)-boronic acid (0.014 mol) and the intermediate 5 (0.014 mol) were added to a solution of 1,4-dioxane-2,5-diol (0.014 mol) in EtOH (175 ml). The mixture was stirred at room temperature for 24 hours. EtOH was evaporated. The residue was taken up in DCM/H₂O, NaHCO₃ was added. The mixture was extracted with DCM. The organic layer was separated, dried (MgSO₄), filtered and the solvent was evaporated. The residue (6.6 g) was purified by column chromatography over silica gel (20-45 μm) (eluent: DCM/MeOH/NH₄OH 98/2/0.1). Three fractions were collected and the solvent was evaporated, yielding 1.5 g of intermediate 6.

d) Preparation of intermediate 7

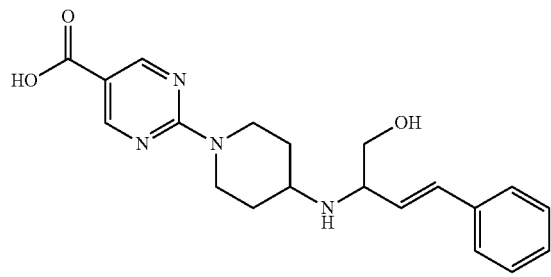

A mixture of intermediate 6 (0.0037 mol) and lithium hydroxide monohydrate (0.0113 mol) in THF (50 ml) and water (25 ml) was stirred at room temperature for 48 hours. Hydrochloric acid 1N (15 ml) was added. The mixture was evaporated till dryness, yielding intermediate 7. This product was used directly in the next reaction step.

e) Preparation of intermediate 8

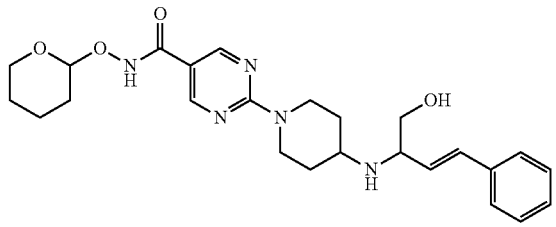

1-hydroxy-1H-benzotriazole (0.0056 mol) then N'-(ethyl-carbonimidoyl)-N,N-dimethyl-1,3-propanediamine (0.0056 mol) and O-(tetrahydro-2H-pyran-2-yl)-hydroxylamine (0.0056 mol) were added at room temperature to a solution of intermediate 7 (0.0037 mol) and triethylamine (0.0113 mol) in DCM/THF (200 ml) under N₂ flow. The mixture was stirred at room temperature for 3 hours, then stirred at 45° C. for 72 hours, poured out into water and extracted with DCM. The organic layer was separated, dried (MgSO₄), filtered and the solvent was evaporated. The residue (2.4 g) was purified by column chromatography over silica gel (15-40 μm) (eluent: DCM/MeOH/NH₄OH 94/6/0.1). The pure fractions were collected and the solvent was evaporated. The residue (0.43 g) was crystallized from DIPE/2-propanone. The precipitate was filtered off and dried, yielding 0.19 g (11%) of intermediate 8.

Example A3 a) Preparation of intermediate 9

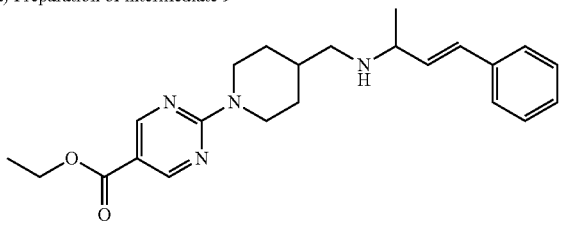

Titanium (IV) ethoxide (0.0052 mol) was added at room temperature to a solution of 2-(4-aminomethyl-piperidin-1-yl)-pyrimidine-5-carboxylic acid ethyl ester (0.0026 mol) and 4-phenyl-3-buten-2-one in 1,2-dichloro-ethane (30 ml) under N₂ flow. The mixture was stirred at room temperature for 48 hours. Sodium triacetoxyborohydride (0.0052 mol) was added. The mixture was stirred at room temperature for 6 hours, poured out into ice water and filtered over celite. The organic layer was separated, dried (MgSO₄), filtered and the solvent was evaporated. The residue (1 g) was purified by column chromatography over silica gel (15-40 μm) (eluent: DCM/MeOH/NH₄OH 96/4/0.2). The pure fractions were collected and the solvent was evaporated. The residue (0.6 g) was crystallized from DIPE. The precipitate was filtered off and dried, yielding 0.545 g (53%) of intermediate 9, melting point 79° C.

b) Preparation of intermediate 10

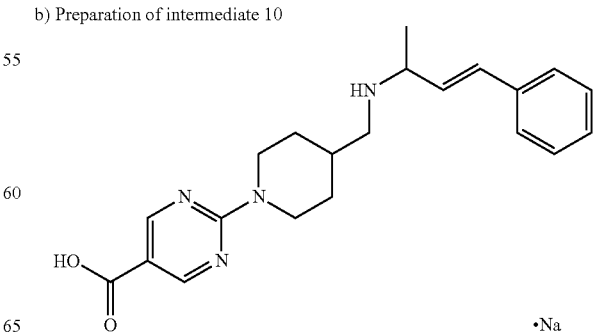

A mixture of intermediate 9 (0.0012 mol) and sodium hydroxide (0.0049 mol) in EtOH (50 ml) was stirred and refluxed for 6 hours, then cooled to room temperature and the solvent was evaporated till dryness. The residue was taken up in diethyl ether. The precipitate was filtered off and dried, yielding 0.537 g (>100%) of intermediate 10, melting point >260° C.

c) Preparation of intermediate 11

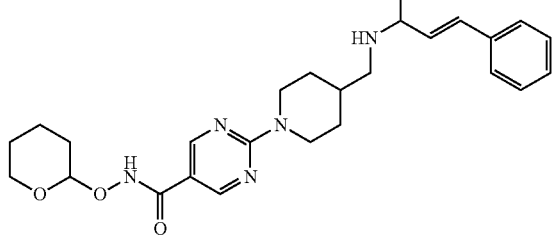

1-hydroxy-1H-benzotriazole (0.0028 mol) then N'-(ethylcarbonimidoyl)-N,N-dimethyl-1,3-propanediamine (0.0028 mol) were added at room temperature to a solution of intermediate 10 in THF (55 ml) and DCM (55 ml) under $N_2$ flow. The mixture was stirred at room temperature for 30 minutes. O-(tetrahydro-2H-pyran-2-yl)-hydroxylamine (0.0028 mol) was added. The mixture was stirred at room temperature for 48 hours, poured out into water and extracted with DCM. The organic layer was separated, dried (MgSO$_4$), filtered and the solvent was evaporated. The residue (0.8 g) was purified by column chromatography over silica gel (10 μm) (eluent: DCM/MeOH/NH4OH 95/5/0.1). The pure fractions were collected and the solvent was evaporated. The residue (0.295 g, 46%) was crystallized from DIPE; The precipitate was filtered off and dried, yielding 0.282 g (43%) of intermediate 11, melting point 80° C.

Example A4 a) Preparation of intermediate 12

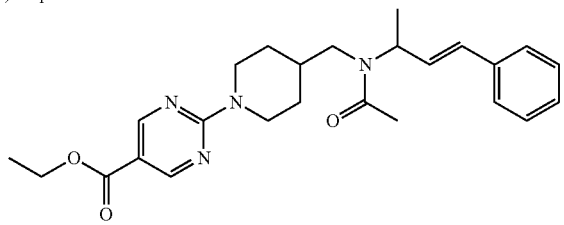

A solution of acetyl chloride (0.0015 mol) in DCM (2 ml) was added dropwise to a solution of intermediate 9 and triethylamine (0.003 mol) in DCM (20 ml). The mixture was cooled to 5° C. under $N_2$ flow, stirred at 5° C. for 30 minutes, then stirred at room temperature for 3 hours, poured out into ice water and extracted with DCM. The organic layer was separated, dried (MgSO$_4$), filtered and the solvent was evaporated. The residue (0.43 g) was purified by column chromatography over silica gel (15-40 μm) (eluent: DCM/MeOH/ NH$_4$OH 98/2/0.1). The pure fractions were collected and the solvent was evaporated, yielding 0.38 g (86%) of intermediate 12.

b) Preparation of intermediate 13

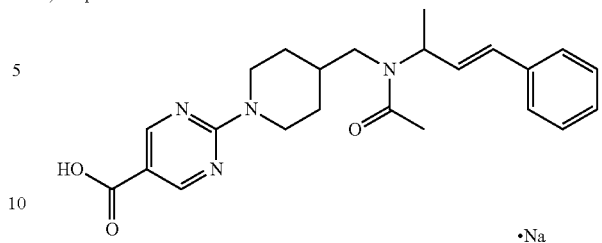

A mixture of intermediate 12 (0.0008 mol) and sodium hydroxide (0.0034 mol) in EtOH (40 ml) was stirred and refluxed for 15 hours, then evaporated till dryness, yielding 0.37 g of intermediate 13. This fraction was used directly in the next reaction step.

c) Preparation of intermediate 14

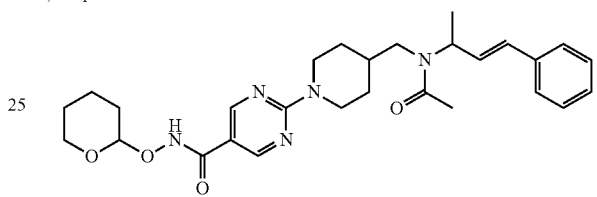

1-hydroxy-1H-benzotriazole (0.0013 mol) and N'-(ethylcarbonimidoyl)-N,N-dimethyl-1,3-propanediamine (0.0013 mol) were added at room temperature to a solution of intermediate 13 (0.0008 mol) and O-(tetrahydro-2H-pyran-2-yl)-hydroxylamine (0.0013 mol) in DCM/THF (50 ml/50 ml) under $N_2$ flow. The mixture was stirred at room temperature for 5 days, poured out into water and extracted with DCM. The organic layer was separated, dried (MgSO$_4$), filtered and the solvent was evaporated. The residue (0.79 g) was purified by column chromatography over silica gel (15-40 μm) (eluent: DCM/MeOH/NH4OH 99/1/0.5 to 92/8/0.5). The pure fractions were collected and the solvent was evaporated, yielding 0.235 g (53%) of intermediate 14.

Example A5 a) Preparation of intermediate 15

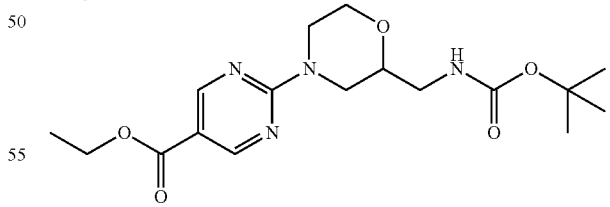

A solution of 2-(methylsulfonyl)-5-pyrimidinecarboxylic acid, ethyl ester (0.0118 mol) in acetonitrile (30 ml) was added dropwise to a solution of (2-morpholinylmethyl)-carbamic acid, 1,1-dimethylethyl ester (0.0098 mol) and potassium carbonate (0.0196 mol) in acetonitrile (80 ml) under $N_2$ flow. The mixture was stirred at room temperature for 12 hours, poured out into water and extracted with EtOAc. The organic layer was separated, dried (MgSO$_4$), filtered, and the solvent was evaporated till dryness. The residue (5.6 g) was purified by column chromatography over silica gel (15-35 µm) (eluent: DCM/MeOH 99/1). Two fractions were collected and the solvent was evaporated. The residue (0.75 g) was crystallized from diethyl ether. The precipitate was filtered off and dried, yielding 0.3 g of intermediate 15, melting point 100° C.

b) Preparation of intermediate 16

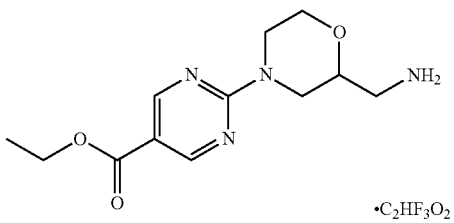

TFA (7.5 ml) was added at 0° C. to a mixture of intermediate 15 (0.037 mol) in DCM (150 ml). The mixture was stirred at room temperature for 48 hours. The solvent was evaporated. Diethyl ether was added. The precipitate was filtered off and dried, yielding 13.5 g (96%) of intermediate 16, melting point 180° C.

c) Preparation of intermediate 17

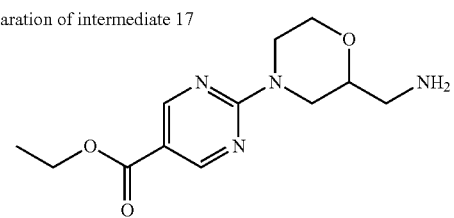

Intermediate 16 (0.0105 mol) was added to an aqueous solution of potassium carbonate 10% (100 ml) in DCM (100 ml). The mixture was stirred at room temperature for 15 minutes, then extracted with DCM. The organic layer was separated, dried (MRSO$_4$), filtered and the solvent was evaporated, yielding 2.6 g of intermediate 17.

d) Preparation of intermediate 18

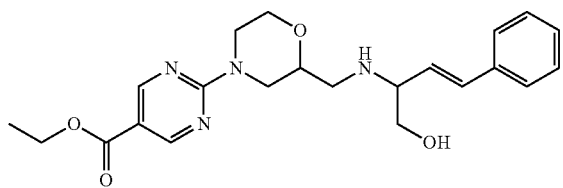

A mixture of intermediate 17 (0.0093 mol), [(1E)-2-phenylethenyl]-boronic acid (0.0031 mol) and 1,4-dioxane-2,5-diol (0.0031 mol) in EtOH (125 ml) was stirred at room temperature for 4 days, then evaporated till dryness. The mixture was taken up in EtOAc. The mixture was washed with water, then with saturated NaCl. The organic layer was separated, dried (MgSO$_4$), filtered and the solvent was evaporated. The residue (3.3 g) was purified by column chromatography over silica gel (15-40 µm) (eluent: DCM/MeOH/ NH$_4$OH 95/5/0.1). The pure fractions were collected and the solvent was evaporated. The residue (0.95 g) was crystallized from DIPE. The precipitate was filtered off and dried, yielding 0.3 g of intermediate 18, melting point 146° C.

e) Preparation of intermediate 19

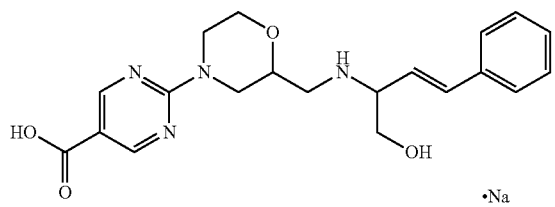

A mixture of intermediate 18 (0.001 mol) and sodium hydroxide (0.002 mol) in EtOH (10 ml) was stirred at 70° C. for 6 hours, then evaporated till dryness. The residue was taken up in acetonitrile several times, then evaporated till dryness, yielding intermediate 19. This product was used directly in the next reaction step.

f) Preparation of intermediate 20

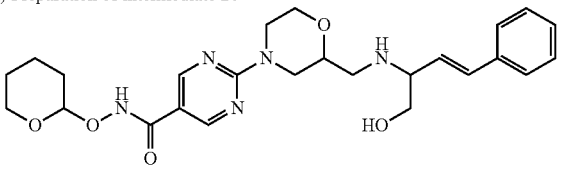

HOBT (0.0025 mol) then EDC (0.0025 mol) were added at room temperature to a solution of intermediate 19 (0.001 mol) and O-(tetrahydro-2H-pyran-2-yl)-hydroxylamine (0.0025 mol) in DCM-THF (100 ml) under N$_2$ flow. The mixture was stirred at room temperature for 48 hours, poured out into water and extracted with DCM. The organic layer was separated, dried (MgSO$_4$), filtered and the solvent was evaporated. The residue (0.65 g) was purified by column chromatography over silica gel (5 µm) (eluent: DCM/MeOH/NH$_4$OH 98/2/0.2 to 90/10/1). The pure fractions were collected and the solvent was evaporated, yielding 0.26 g (54%) of intermediate 20.

Example A6 a) Preparation of intermediate 21

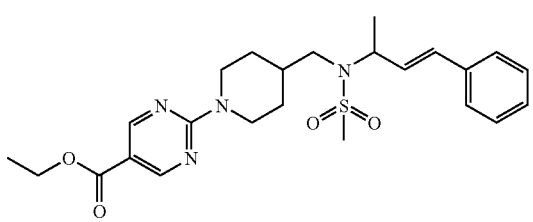

Methanesulfonyl chloride (0.0012 mol) was added at room temperature to a solution of intermediate 9 (0.0008 mol) and triethylamine (0.0025 mol) in DCM (20 ml) under N$_2$ flow. The mixture was stirred for 15 hours. The organic layer was washed with water, dried (MgSO$_4$), filtered and the solvent was evaporated. The residue (0.5 g) was crystallized from DIPE. The precipitate was filtered off and dried, yielding 0.3 g (73%) of intermediate 21, melting point 128° C.

b) Preparation of intermediate 22

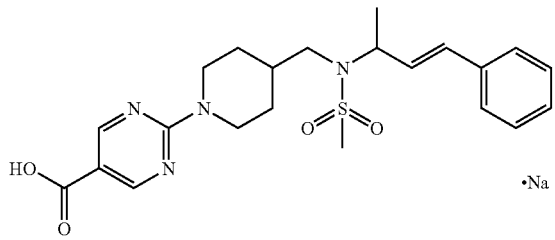

A mixture of intermediate 21 (0.0006 mol) and sodium hydroxide (0.0025 mol) in EtOH (40 ml) was stirred and refluxed for 15 hours, then evaporated till dryness, yielding intermediate 22. This product was used directly in the next reaction step.

c) Preparation of intermediate 23

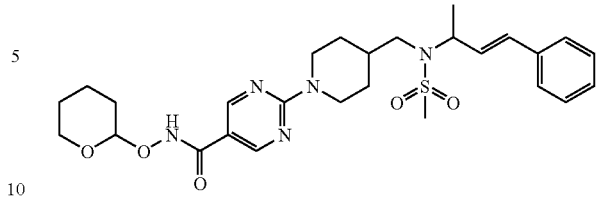

HOBT (0.0012 mol) then EDC (0.0012 mol) were added at room temperature to a solution of intermediate 22 (0.0006 mol) and O-(tetrahydro-2H-pyran-2-yl)-hydroxylamine (0.0012 mol) in DCM/THF (100 ml). The mixture was stirred at room temperature for 72 hours, poured out on ice and extracted with DCM. The organic layer was separated, dried (MgSO$_4$), filtered and the solvent was evaporated. The residue (0.65 g) was purified by column chromatography over silica gel (10 μm) (eluent: DCM/MeOH/NH4OH 99/1/0.1). The pure fractions were collected and the solvent was evaporated, yielding 0.2 g (59%) of intermediate 23.

Table F-1 lists the intermediates that were prepared in the above Examples.

TABLE F-1

(intermediates)

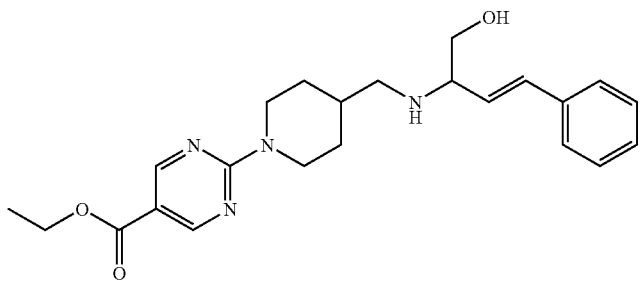

(E); Interm. 1; Ex. [A1]

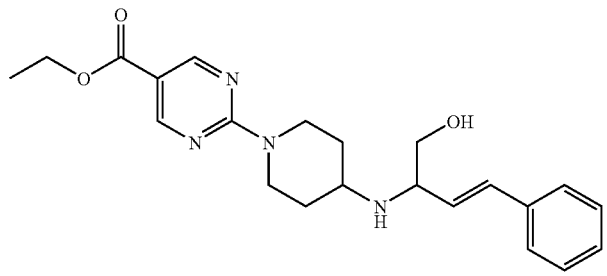

(E); Interm. 6; Ex. [A2]

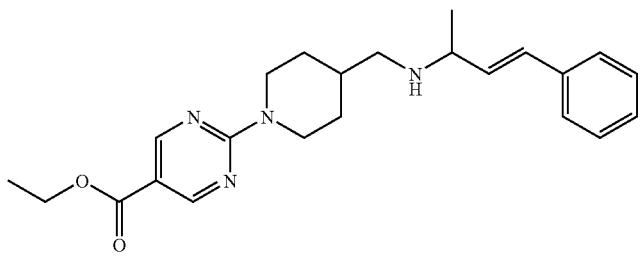

(E); Interm. 9; Ex. [A3]; mp. 79° C.

TABLE F-1-continued (intermediates)

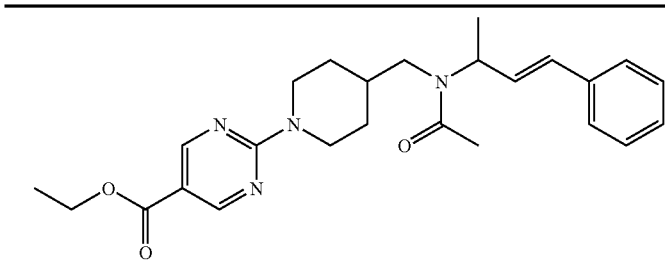

(E); interm. 12; Ex. [A4];

B. Preparation of the Final Compounds

Example B1

Preparation of compound 1

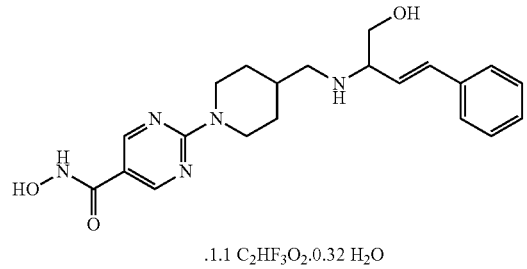

.1.1 C$_2$HF$_3$O$_2$.0.32 H$_2$O

A mixture of intermediate 3 (0.0002 mol) in TFA (0.47 ml) and MeOH (9.5 ml) was stirred at room temperature for 48 hours and then the solvent was evaporated. The residue was crystallized from diethylether/MeOH. The precipitate was filtered off and dried, yielding 0.073 g (70%) of compound 1, melting point 196° C.

Example B2

Preparation of compound 2

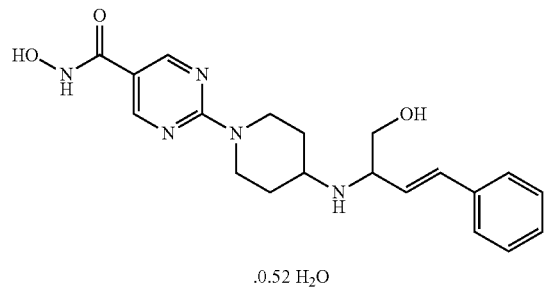

.0.52 H$_2$O

A mixture of intermediate 8 (0.0003 mol) in trifluoroacetic acid (0.9 ml) and MeOH (18 ml) was stirred at room temperature for 24 hours. The residue (0.28 g) was purified by column chromatography over silica gel (15-40 µm) (eluent: DCM/MeOH/H$_2$O 80/20/2). The pure fractions were collected and the solvent was evaporated. The residue (0.12 g) was crystallized from DIPE. The precipitate was filtered off and dried, yielding 0.11 g (73%) of compound 2, melting point 109° C.

Example B3

Preparation of compound 3

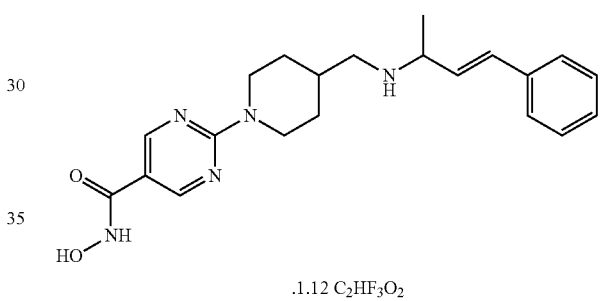

.1.12 C$_2$HF$_3$O$_2$

A mixture of intermediate 11 (0.0005 mol) in TFA (1 ml) and MeOH (30 ml) was stirred at room temperature for 3 days and then the solvent was evaporated. The residue was crystallized from diethylether. The precipitate was filtered off and dried, yielding 0.23 g (82%) of compound 3, melting point 155° C.

Example B4

Preparation of compound 4

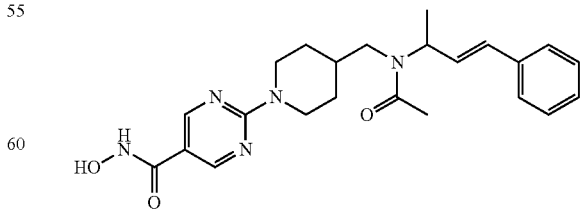

A mixture of intermediate 14 (0.0005 mol) in TFA (1.15 ml) and MeOH (23 ml) was stirred at room temperature for 24 hours and then the solvent was evaporated. The residue was crystallized from diethylether. The precipitate was filtered off and dried, yielding 0.135 g (71%) of compound 4, melting point 100° C.

Example B5

Preparation of compound 5

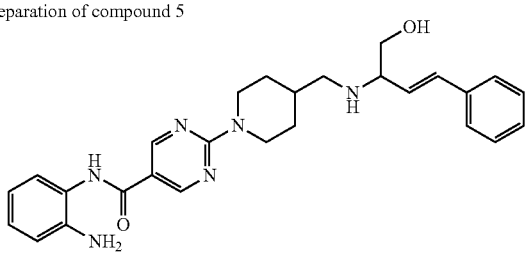

PyBOP (0.004 mol), then triethylamine (0.008 mol) then 1,2-benzenediamine, monohydrochloride (0.007 mol) were added to a solution of intermediate 2 (0.002 mol) in DCM/THF (200 ml). The mixture was stirred for 48 hours, poured out into water and extracted with DCM. The organic layer was separated, dried (MgSO$_4$), filtered and the solvent was evaporated. The residue (4.4 g) was purified by column chromatography over silica gel (15-40 μm) (eluent: DCM/MeOH/NH$_4$OH 93/7/0.1). The pure fractions were collected and the solvent was evaporated. The residue (0.46 g) was crystallized from EtOAc. The precipitate was filtered off and dried, yielding 0.13 g (14%) of compound 5, melting point 178° C.

Example B6

Preparation of compound 6

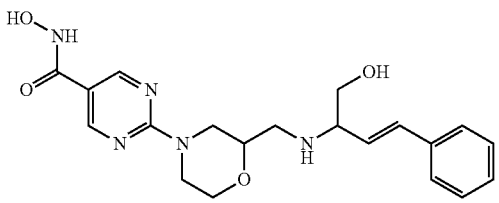

TFA (1.3 ml) was added dropwise at 5° C. to a solution of intermediate 20 (0.0005 mol) in MeOH (26 ml). The mixture was stirred at room temperature for 48 hours, then evaporated till dryness. The residue (0.3 g) was purified by column chromatography over amino coated silica gel (25-40 μm) (eluent: DCM/MeOH/H$_2$O 90/10/1). The pure fractions were collected and the solvent was evaporated. The residue (0.17 g) was crystallized from diethyl ether. The precipitate was filtered off and dried, yielding 0.145 g of compound 6, melting point 111° C.

Example B7

Preparation of compound 7

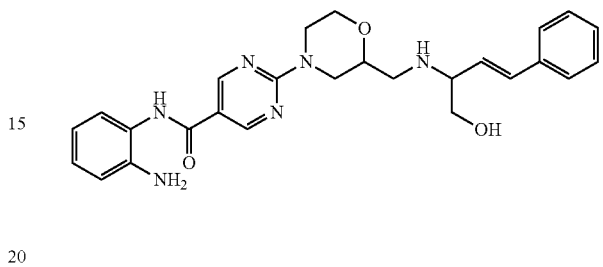

PyBOP (0.0046 mol) then triethylamine (0.0091 mol) then 1,2-benzenediamine, monohydrochloride (0.008 mol) were added at room temperature to a solution of intermediate 19 (0.0022 mol) in DCM/THF (50/50) (200 ml). The mixture was stirred at room temperature, poured out into water and extracted with DCM. The organic layer was separated, dried (MgSO$_4$), filtered, and the solvent was evaporated till dryness. The residue (5 g) was purified by column chromatography over silica gel (15-40 μm) (eluent: DCM/MeOH/NH$_4$OH 95/5/0.1). The pure fractions were collected and the solvent was evaporated. The residue (0.19 g) was crystallized from DIPE. The precipitate was filtered off and dried, yielding: 0.17 g (16%) of compound 7, melting point 95° C.

Example B8

Preparation of compound 8

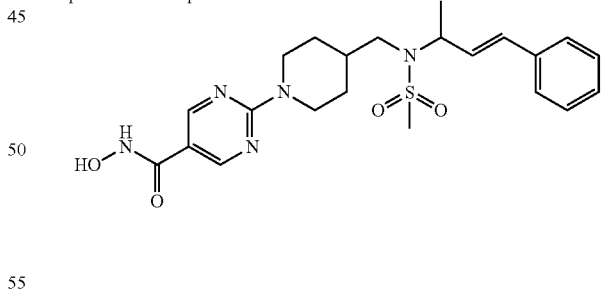

TFA (0.48 ml) was added dropwise to a solution of intermediate 23 (0.0003 mol) in MeOH (19 ml). The mixture was cooled to 5° C., then stirred at room temperature for 24 hours and evaporated till dryness. The residue was crystallized from diethyl ether. The precipitate was filtered off and dried, yielding 0.11 g of compound 8, melting point 110° C.

Table F-2 lists the compounds that were prepared in the above Examples. The following abbreviations were used in the tables: .C$_2$HF$_3$O$_2$ stands for the trifluoroacetate salt.

TABLE F-2
(final compounds)
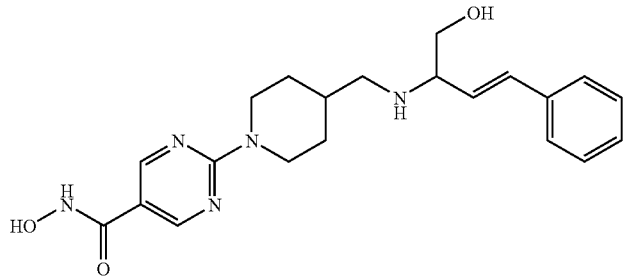
(E) 1.1 C₂HF₃O₂. 0.32 H₂O; Co. No. 1; Ex. [B1]; mp. 196° C.
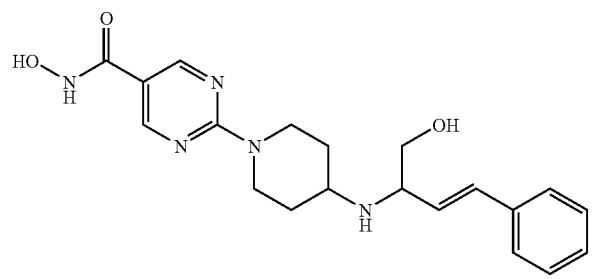
(E) .0.52 H₂O; Co. No. 2; Ex. [B2]; mp. 109° C.
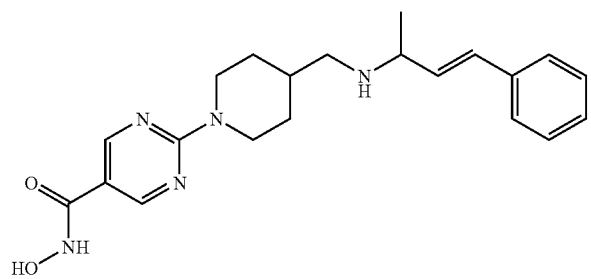
(E) 1.12 C₂HF₃O₂; Co. No. 3; Ex. [B3]; mp. 155° C.
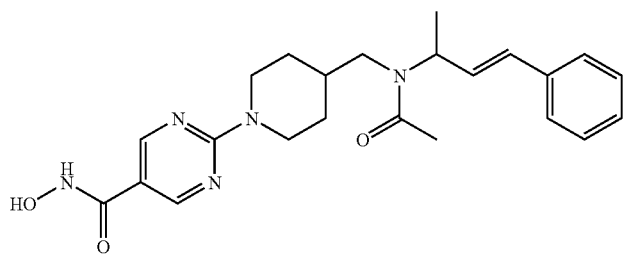
(E); Co. No. 4; Ex. [B4]; mp. 100° C.

TABLE F-2-continued (final compounds)

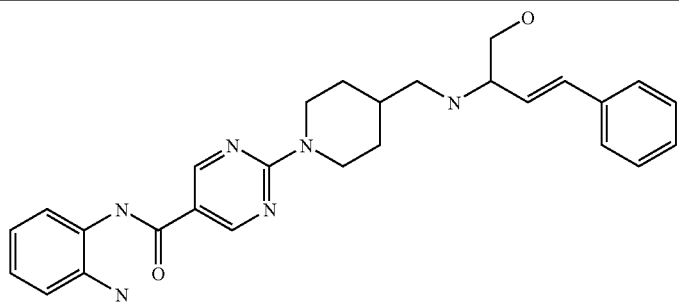

(E); Co. No. 5; Ex. [B5]; mp. 178° C.

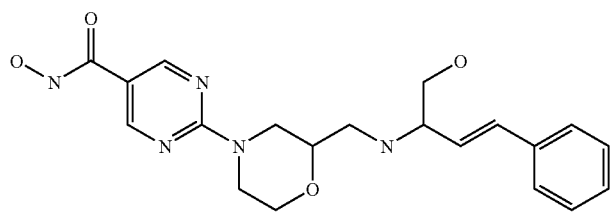

(E); Co. No. 6; Ex. [B6]; mp. 111° C.

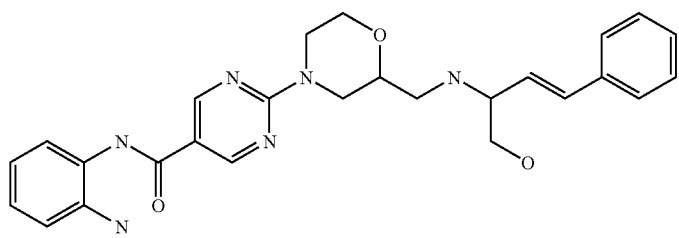

(E); Co. No. 7; Ex. [B7]; mp. 95° C.

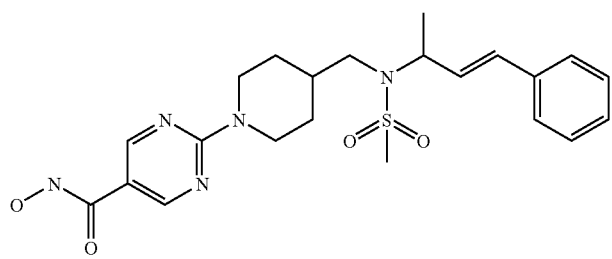

(E); Co. No. 8; Ex. [B8]; mp. 110° C.

C. Pharmacological Example

The in vitro assay for inhibition of histone deacetylase (see example C.1) measures the inhibition of HDAC enzymatic activity obtained with the compounds of formula (I).

Cellular activity of the compounds of formula (I) was determined on A2780 tumour cells using a colorimetric assay for cell toxicity or survival (Mosmann Tim, Journal of Immunological Methods 65: 55-63, 1983) (see example C.2).

The solubility of a compound measures the ability of a compound to stay in solution. The solubility of a compound at different pH's can be measured with the use of a chemiluminescent nitrogen detector (see example C.3).

A drug's permeability expresses its ability to move from one medium into or through another. Specifically its ability to move through the intestinal membrane into the blood stream and/or from the blood stream into the target. Permeability (see example C.4) can be measured through the formation of a filter-immobilized artificial membrane phospholipid bilayer. In the filter-immobilized artificial membrane assay, a "sandwich" is formed with a 96-well microtitre plate and a 96-well filter plate, such that each composite well is divided into two chambers with a donor solution at the bottom and an acceptor solution at the top, separated by a 125 μm microfilter disc (0.45 μm pores), coated with 2% (wt/v) dodecane solution of dioleoylphosphatidyl-choline, under conditions that multi-lamellar bilayers form inside the filter channels when the system contacts an aqueous buffer solution. The permeability of compounds through this artificial membrane is measured in cm/s. The purpose is to look for the permeation of the drugs through a parallel artificial membrane at 2 different pH's: 4.0 and 7.4. Compound detection is done with UV-spectrometry at optimal wavelength between 250 and 500 nm.

Metabolism of drugs means that a lipid-soluble xenobiotic or endobiotic compound is enzymatically transformed into (a) polar, water-soluble, and excretable metabolite(s). The major organ for drug metabolism is the liver. The metabolic products are often less active than the parent drug or inactive. However, some metabolites may have enhanced activity or toxic effects. Thus drug metabolism may include both "detoxication" and "toxication" processes. One of the major enzyme systems that determine the organism's capability of dealing with drugs and chemicals is represented by the cytochrome P450 monooxygenases, which are NADPH dependent enzymes. Metabolic stability of compounds can be determined in vitro with the use of subcellular human tissue (see example C.5.a.). Here metabolic stability of the compounds is expressed as % of drug metabolised after 15 minutes incubation of these compounds with microsomes. Quantitation of the compounds was determined by LC-MS analysis. Metabolic stability of compounds can also be determined by calculating the half live of compounds in rat hepatocyte cells (see example C.5.b.).

It has been shown that a wide variety of anti-tumoral agents activate the p21 protein, including DNA damaging agents and histone deacetylase inhibitors. DNA damaging agents activate the p21 gene through the tumour suppressor p53, while histone deacetylase inhibitors transcriptionally activates the p21 gene via the transcription factor Sp1. Thus, DNA damaging agents activate the p21 promoter through the p53 responsive element while histone deacetylase inhibitors activate the p21 promoter through sp1 sites (located at the −60 bp to +40 bp region relative to the TATA box) both leading to increased expression of the p21 protein. When the p21 promoter in a cells consists of a p21 1300 bp promoter fragment that does not comprise the p53 responsive elements it is accordingly non-responsive to DNA damaging agents. The capacity of compounds to induce p21 can be evaluated in several ways. A first method tests the capacity of compounds to induce p21 as the consequence of HDAC inhibition at the cellular level. The cells can be stably transfected with an expression vector containing a p21 1300 bp promoter fragment that does not comprise the p53 responsive elements and wherein an increase of a reporter gene expression, compared to the control levels, identifies the compound as having p21 induction capacity. The reporter gene is a fluorescent protein and the expression of the reporter gene is measured as the amount of fluorescent light emitted (see example C.6.a.). The second method is an in vivo method wherein mice are used for screening the pharmaceutical activity of a compound. The above described stably transformed tumour cells can be administered to mice in an amount sufficient to effect production of a tumour. After the tumour cells had sufficient time to form a tumour, a potentially active compound can be administered to the animals and the effect of said compound on the tumour cells is evaluated by measuring the expression of the reporter gene. Incubation with pharmaceutical active compounds will result in an increase of reporter gene expression compared to the control levels (see example C.6.b.)

Specific HDAC inhibitors should not inhibit other enzymes like the abundant CYP P450 proteins. The CYP P450 (*E. coli* expressed) proteins 3A4, 2D6 en 2C9 convert their specific substrates into a fluorescent molecule. The CYP3A4 protein converts 7-benzyloxy-trifluoromethyl coumarin (BFC) into 7-hydroxy-trifluoromethyl coumarin. The CYP2D6 protein converts 3-[2-(N,N-diethyl-N-methylamino)ethyl]-7-methoxy-4-methylcoumarin (AMMC) into 3-[2-(N,N-diethylamino)ethyl]-7-hydroxy-4-methylcoumarin hydrochloride and the CYP2C9 protein converts 7-Methoxy-4-trifluoromethyl coumarin (MFC) into 7-hydroxy-trifluoromethyl coumarin. Compounds inhibiting the enzymatic reaction will result in a decrease of fluorescent signal (see example C.7).

Example C.1

In Vitro Assay for Inhibition of Histone Deacetylase

The HDAC Fluorescent Activity Assay/Drug Discovery Kit of Biomol (cat. No: AK-500-0001) was used. The HDAC Fluorescent Activity Assay is based on the Fluor de Lys (Fluorogenic Histone deAcetylase Lysyl) substrate and developer combination. The Fluor de Lys substrate, comprises an acetylated lysine side chain. Deacetylation of the substrate sensitizes the substrate so that, in the second step, treatment with the Fluor de Lys developer produces a fluorophore.

HeLa nuclear extracts (supplier: Biomol) were incubated at 60 µg/ml with 75 µM of substrate. The Fluor de Lys substrate was added in a buffer containing 25 mM Tris, 137 mM NaCl, 2.7 mM KCl and 1 mM $MgCl_2.6H_2O$ at pH 7.4. After 30 min, 1 volume of the developer was added. The fluorophore was excited with 355 nm light and the emitted light (450 nm) was be detected on a fluorometric plate reader.

For each experiment, controls (containing HeLa nuclear extract and buffer), a blank incubation (containing buffer but no HeLa nuclear extract) and samples (containing compound dissolved in DMSO and further diluted in buffer and HeLa nuclear extract) were run in parallel. In first instance, compounds were tested at a concentration of $10^{-5}$M. When the compounds showed activity at $10^{-5}$M, a concentration-response curve was made wherein the compounds were tested at concentrations between $10^{-5}$M and $10^{-9}$M. All sample were tested 4 times. In each test the blank value was substracted from both the control and the sample values. The control sample represented 100% of substrate deactylation. For each sample the fluorescence was expressed as a percentage of the mean value of the controls. When appropriate $IC_{50}$-values (concentration of the drug, needed to reduce the amount of metabolites to 50% of the control) were computed using probit analysis for graded data. Herein the effects of test compounds are expressed as $pIC_{50}$ (the negative log value of the $IC_{50}$-value) (see Table F-3).

Example C.2

Determination of Antiproliferative Activity on A2780 Cells

All compounds tested were dissolved in DMSO and further dilutions were made in culture medium. Final DMSO concentrations never exceeded 0.1% (v/v) in cell proliferation assays. Controls contained A2780 cells and DMSO without compound and blanks contained DMSO but no cells. MTT was dissolved at 5 mg/ml in PBS. A glycine buffer comprised of 0.1 M glycine and 0.1 M NaCl buffered to pH 10.5 with NaOH (1 N) was prepared (all reagents were from Merck).

The human A2790 ovarian carcinoma cells (a kind gift from Dr. T. C. Hamilton [Fox Chase Cancer Centre, Pennsylvania, USA]) were cultured in RPMI 1640 medium supplemented with 2 mM L-glutamine, 50 µg/ml gentamicin and 10% fetal calf serum. Cells were routinely kept as monolayer cultures at 37° C. in a humidified 5% $CO_2$ atmosphere. Cells were passaged once a week using a trypsin/EDTA solution at a split ratio of 1:40. All media and supplements were obtained from Life Technologies. Cells were free of mycoplasma contamination as determined using the Gen-Probe Mycoplasma Tissue Culture kit (supplier: BioMérieux).

Cells were seeded in NUNC™ 96-well culture plates (Supplier: Life Technologies) and allowed to adhere to the plastic overnight. Densities used for plating were 1500 cells per well in a total volume of 200 µl medium. After cell adhesion to the plates, medium was changed and drugs and/or solvents were added to a final volume of 200 µl. Following four days of incubation, medium was replaced by 200 µl fresh medium and cell density and viability was assessed using an MTT-based assay. To each well, 25 µl MTT solution was added and the cells were further incubated for 2 hours at 37° C. The medium was then carefully aspirated and the blue MTT-formazan product was solubilized by addition of 25 µl glycine buffer followed by 100 µl of DMSO. The microtest plates were shaken for 10 min on a microplate shaker and the absorbance at 540 nm was measured using an Emax 96-well spectrophotometer (Supplier: Sopachem). Within an experiment, the results for each experimental condition are the mean of 3 replicate wells. For initial screening purposes, compounds were tested at a single fixed concentration of $10^{-6}$ M. For active compounds, the experiments were repeated to establish full concentration-response curves. For each experiment, controls (containing no drug) and a blank incubation (containing no cells or drugs) were run in parallel. The blank value was subtracted from all control and sample values. For each sample, the mean value for cell growth (in absorbance units) was expressed as a percentage of the mean value for cell growth of the control. When appropriate, $IC_{50}$-values (concentration of the drug, needed to reduce cell growth to 50% of the control) were computed using probit analysis for graded data (Finney, D. J., Probit Analyses, $2^{nd}$ Ed. Chapter 10, Graded Responses, Cambridge University Press, Cambridge 1962). Herein the effects of test compounds are expressed as $pIC_{50}$ (the negative log value of the $IC_{50}$-value)(see Table F-3).

Example C.3

Solubility/Stability

The solubility of a compound, at different pH's, can be measured with the use of a chemiluminescent nitrogen detector. Compound No. 2 showed a solubility in water >0.5 mg/ml; compound No. 3 showed a solubility in water >1 mg/ml and compound No. 4 showed a solubility in water >0.1 mg/ml.

Example C.4

Parallel Artificial Membrane Permeability Analysis

The stock samples (aliquots of 10 µl of a stock solution of 5 mM in 100% DMSO) were diluted in a deep-well or Pre-mix plate containing 2 ml of an aqueous buffer system pH 4 or pH 7.4 (PSR4 System Solution Concentrate (pION)).

Before samples were added to the reference plate, 150 µl of buffer was added to wells and a blank UV-measurement was performed. Thereafter the buffer was discarded and the plate was used as reference plate. All measurements were done in UV-resistant plates (supplier: Costar or Greiner).

After the blank measurement of the reference plate, 150 µl of the diluted samples was added to the reference plate and 200 µl of the diluted samples was added to donorplate 1. An acceptor filter plate 1 (supplier: Millipore, type: MAIP N45) was coated with 4 µl of the artificial membrane-forming solution (1,2-Dioleoyl-sn-Glycer-3-Phosphocholine in Dodecane containing 0.1% 2,6-Di-tert-butyl-4-methylphenol and placed on top of donor plate 1 to form a "sandwich". Buffer (200 µl) was dispensed into the acceptor wells on the top. The sandwich was covered with a lid and stored for 18 h at room temperature in the dark.

A blank measurement of acceptor plate 2 was performed through the addition of 150 µl of buffer to the wells, followed by an UV-measurement. After the blank measurement of acceptor plate 2 the buffer was discarded and 150 µl of acceptor solution was transferred from the acceptor filter plate 1 to the acceptor plate 2. Then the acceptor filter plate 1 was removed form the sandwich. After the blank measurement of donor plate 2 (see above), 150 µl of the donor solution was transferred from donor plate 1 to donor plate 2. The UV spectra of the donor plate 2, acceptor plate 2 and reference plate wells were scanned (with a SpectraMAX 190). All the spectra were processed to calculate permeability with the PSR4p Command Software. All compounds were measured in triplo. Carbamazepine, griseofulvin, acycloguanisine, atenolol, furosemide, and chlorothiazide were used as standards in each experiment. Compounds were ranked in 3 categories as having a low permeability (mean effect<$0.5 \times 10^{-6}$ cm/s; score 1), a medium permeability ($1 \times 10^{-6}$ cm/s>mean effect$\geq 0.5 \times 10^{-6}$ cm/s; score 2) or a high permeability ($\geq 1 \times 10^{-6}$ cm/s; score 3).

Example C.5

Metabolic Stability

Example C.5.a

Sub-cellular tissue preparations were made according to Gorrod et al. (Xenobiotica 5: 453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4) using either a Potter-S (Braun, Italy) equipped with a Teflon pestle or a Sorvall Omni-Mix homogeniser, for 7×10 sec. In both cases, the vessel was kept in/on ice during the homogenization process.

Tissue homogenates were centrifuged at 9000×g for 20 minutes at 4° C. using a Sorvall centrifuge or Beckman Ultracentrifuge. The resulting supernatant was stored at −80° C. and is designated 'S9'.

The S9 fraction can be further centrifuged at 100.000×g for 60 minutes (4° C.) using a Beckman ultracentrifuge. The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 µM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 min at 95 degrees Celsius) microsomes. Recovery of the compounds in the control samples was always 100%.

The mixtures were preincubated for 5 min at 37 degrees Celsius. The reaction was started at timepoint zero (t=0) by addition of 0.8 mM NADP and the samples were incubated for 15 min (t=15). The reaction was terminated by the addition of 2 volumes of DMSO. Then the samples were centrifuged for 10 min at 900×g and the supernatants were stored at room temperature for no longer as 24 h before analysis. All incubations were performed in duplo. Analysis of the supernatants was performed with LC-MS analysis. Elution of the samples was performed on a Xterra MS C18 (50×4.6 mm, 5 μm, Waters, US). An Alliance 2790 (Supplier: Waters, US) HPLC system was used. Elution was with buffer A (25 mM ammoniumacetate (pH 5.2) in $H_2O$/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 min a linear fashion and organic phase concentration was kept stationary for an additional 1.5 min. Total injection volume of the samples was 25 μl.

A Quattro (supplier: Micromass, Manchester, UK) triple quadrupole mass spectrometer fitted with and ESI source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 sec.

Metabolic stability was expressed as % metabolism of the compound after 15 min of incubation in the presence of active microsomes (E(act)) (% metabolism=100%–

$$\left(\left(\frac{\text{Total Ion Current } (TIC) \text{ of } E(\text{act}) \text{ at } t = 15}{TIC \text{ of } E(\text{act}) \text{ at } t = 0}\right) \times 100\right).$$

Compounds that had a percentage metabolism less than 20% were defined as highly metabolic stable. Compound that had a metabolism between 20 and 70% were defined as intermediately stable and compounds that showed a percentage metabolism higher than 70 were defined as low metabolic stable. Three reference compounds were always included whenever a metabolic stability screening was performed. Verapamil was included as a compound with low metabolic stability (% metabolism=73%). Cisapride was included as a compound with medium metabolic stability (% metabolism 45%) and propanol was included as a compound with intermediate to high metabolic stability (25% metabolism). These reference compounds were used to validate the metabolic stability assay.

C.5.b

Metabolic Stability with Rat Hepatocytes Cell Culture

Rat hepatocytes were isolated from male Sprague Dowley rats. The compounds were dissolved to a 5 mM stock solution in 100% DMSO and incubated at a final concentration of 5 μM for 0, 15, 30, 60 and 120 min with rat hepatocyte cell cultures (0.5 million viable cells/0.5 ml) using 24-well plates.

Samples were prepared for LC-MS by addition of two volumes of DMSO. The samples were thoroughly shaken and subsequently centrifuged at 900 g for 10 min (room temperature). All experiments were performed in triplicate. Of the resulting supernatant 50 μl was analysed by LC-MS.

For LC-MS, elution of samples was performed on a Hypersil BDS C18 column (50×4.6 mm, 5 μm, Thermohypersil, UK). The HPLC system comprised a Surveyor delivery system (Surveyor Inc., San Jose, US) equipped with a Surveyor autosampler device. Elution was with buffer A (10 mM ammoniumacetate (pH 6.9) in $H_2O$/Acetonitrile (95:5)) and solvent B (acetonitrile) at a flow rate of 1.2 ml/min. The gradient employed was 0.5 min solvent A as start condition followed by increasing the organic phase concentration from 0% B till 95% B over 2 min in a linear fashion. This phase was kept stationary for a further 2 min and reduced again to 0% B within 0.5 min.

Total injection volume of samples was 50 μL. Column oven temperature was kept at 40° C. The LC flow was splitted for MS detection and 0.1 ml let into the source. An triple quadrupol mass spectrometer TSQ Quantum (Thermofinnigan, LaJolla, USA) mass spectrometer fitted with an ESI source was used for detection. Source voltage was set at 3800 volt, the capillary temperature at 300° C. The mass spectrometer was operated in positive ion mode in SIM adjusted to the mass of M+H with a scan width of 1 Da for quantification purposes. Instrument control, data acquisition and processing were performed using the Xcalibur software (ThermoFinnigan, San Jose, Calif., U.S.A). The metabolic stability of compounds in rat hepatocytes was expressed as in vitro half-lives.

As reference, compound R306465 (WO03/76422) was used (in vitro half-live: 8 min). Compound 1 has an in vitro half-live of 103 min.

Example C.6 p21 Induction Capacity

Example C.6.a

Cellular Method

A2780 cells (ATCC) were cultivated in RPMI 1640 medium supplemented with 10% FCS, 2 mM L-glutamine and gentamycine at 37° C. in a humidified incubator with 5% $CO_2$. All cell culture solutions are provided by Gibco-BRL (Gaithersburg, Md.). Other materials are provided by Nunc.

Genomic DNA was extracted from proliferating A2780 cells and used as template for nested PCR isolation of the p21 promoter. The first amplification was performed for 20 cycles at an annealing temperature of 55° C. using the oligonucleotide pair GAGGGCGCGGTGCTTGG and TGCCGC-CGCTCTCTCACC with the genomic DNA as template. The resulting 4.5 kb fragment containing the −4551 to +88 fragment relative to the TATA box was re-amplified with the oligonucleotides TCG GGTACCGAGGGCGCGGTGCTTGG and ATA CTCGAGTGCCGCCGCTCTCTCACC for 20 cycles with annealing at 88° C. resulting in a 4.5 kb fragment and subsequently with the oligonucleotide pair TCG GGTACCGGTAGATGGGAGCGGATAGACACATC and ATACTCGAGTGCCGCCGCTCTCTCACC for 20 cycles with annealing at 88° C. resulting in a 1.3 kb fragment containing the −1300 to +88 fragment relative to the TATA box. The restriction sites XhoI and KpnI present in the oligonucleotides (underlined sequence) were used for subcloning.

The luciferase reporter was removed from the pGL3-basic and replaced by the ZsGreen reporter (from the pZsGreen1-N1 plasmid) at KpnI and XbaI restriction sites. pGL3-basic-ZsGreen-1300 was constructed via insertion of the above mentioned 1.3 kb fragment of the human p21 promoter region into pGL3-basic-ZsGreen at the XhoI and KpnI sites. All restriction enzymes are provided by Boehringer Manheim (Germany). A2780 cells were plated into a 6-well plate at a density of $2 \times 10^5$ cells, incubated for 24 hours, and transfected with 2 ug of pGL3-basic-ZsGreen-1300 and 0.2 ug of pSV2neo vector by using Lipofectamine 2000 (Invitrogen, Brussels, Belgium) as described by manufacturer. The transfected cells were selected for 10 days with G418 (Gibco-BRL, Gaithersburg, Md.) and single cell suspensions were grown. After three weeks, single clones were obtained.

The A2780 selected clones were expanded and seeded at 10000 cells per well into 96-well plates. 24 hours after seeding, the cells were treated for an additional 24 hours with compounds (affecting sp1 sites in the proximal p21 promoter region). Subsequently, cells were fixed with 4% PFA for 30' and counterstained with Hoechst dye. The p21 promoter activation leading to ZsGreen production and thus fluorescence, was monitored by the Ascent Fluoroskan (Thermo Labsystems, Brussels, Belgium).

For each experiment, controls (containing no drug) and a blank incubation (containing no cells or drugs) were run in parallel. The blank value was substracted from all control and sample values. For each sample, the value for p21 induction was expressed as the percentage of the value for p21 present in the control. Percentage induction higher than 130% was defined as significant induction.

Compound 1 was tested and showed significant induction.

Example C.6.b

In Vivo Method

A selected clone was injected subcutaneous ($10^7$ cells/200 µl) into the flank of nude mice and a calliper measurable tumour was obtained after 12 days. From day 12 on, animals were dosed, orally or intraveinally, daily during 6 days with solvent and 20-40 mpk compound (4-10 animals each). Tumours were evaluated for fluorescence by the in-house developed Automated Whole Body Imaging System (Fluorescent stereomicroscope type Olympus® SZX12 equipped with a GFP filter and coupled to a CCD camera type JAI® CV-M90 controlled by a software package based on the IMAQ Vision Software from National Instruments®). As reference, compound R306465 (WO03/76422) was used. Compounds were ranked as inactive (no fluorescence measurable), weaker, identical or better than R306465. Compound 1 was tested and was better than R306465 after oral administration.

Example C.7

P450 Inhibiting Capacity

All compounds tested were dissolved in DMSO (5 mM) and a further dilution to $5 \cdot 10^4$ M was made in acetonitrile. Further dilutions were made in assay buffer (0.1M NaK phosphate buffer pH 7.4) and the final solvent concentration was never higher than 2%.

The assay for the CYP3A4 protein comprises per well 15 pmol P450/mg protein (in 0.00M NaKphosphate buffer+ 1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 µl. After a 5 min pre-incubation at 37° C. the enzymatic reaction was started with the addition of 150 µM of the fluorescent probe substrate BFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Ketoconazole ($IC_{50}$-value=$3\times10^{-8}$M) was included as reference compound in this experiment.

The assay for the CYP2D6 protein comprises per well 6 pmol P450/mg protein (in 0.01M NaKphosphate buffer+ 1.15% KCl), an NADPH generating system (0.41 mM Glucose-6-phosphate, 0.4 U/ml Glucose-6-phosphate dehydrogenase, 0.0082 mM NADP and 0.41 mM $MgCl_2.6H_2O$ in assay buffer) and compound in a total assay volume of 100 µl. After a 5 min pre-incubation at 37° C. the enzymatic reaction was started with the addition of 3 µM of the fluorescent probe substrate AMMC in assay buffer. After an incubation of 45 minutes at room temperature the reaction was terminated after addition of 2 volumes of acetonitrile. Fluorescent determinations were carried out at an excitation wavelength of 405 nm and an emission wavelength of 460 nm. Quinidine ($IC_{50}$-value<$5\times10^{-8}$ M) was included as reference compound in this experiment.

The assay for the CYP2C9 protein comprises per well 15 pmol P450/mg protein (in 0.01 M NaKphosphate buffer+ 1.15% KCl), an NADPH generating system (3.3 mM Glucose-6-phosphate, 0.4 U/ml Glucose-6-phosphate dehydrogenase, 1.3 mM NADP and 3.3 mM $MgCl_2.6H_2O$ in assay buffer) and compound in a total assay volume of 100 µl. After a 5 min pre-incubation at 37° C. the enzymatic reaction was started with the addition of 200 µM of the fluorescent probe substrate MFC in assay buffer. After an incubation of 30 minutes at room temperature the reaction was terminated after addition of 2 volumes of acetonitrile. Fluorescent determinations were carried out at an excitation wavelength of 405 nm and an emission wavelength of 535 nm. Sulfaphenazole ($IC_{50}$-value=$6.8\times10^{-7}$ M) was included as reference compound in this experiment.

For initial screening purposes, compounds were tested at a single fixed concentration of $1\times10^{-5}$ M. For active compounds, the experiments were repeated to establish full concentration-response curves. For each experiment, controls (containing no drug) and a blank incubation (containing no enzyme or drugs) were run in parallel. All compounds were assayed in quadruplicate. The blank value was subtracted from all control and sample values. For each sample, the mean value of P450 activity of the sample (in relative fluorescence units) was expressed as a percentage of the mean value of P450 activity of the control. Percentage inhibition was expressed as 100% minus the mean value of P450 activity of the sample. When appropriate, $IC_{50}$-values (concentration of the drug, needed to reduce P450 activity to 50% of the control) were calculated.

TABLE F-3 lists the results of the compounds that were tested according to example C. 1 and C. 2,

| Co. No. | Enzyme activity pIC50 | Cellular activity pIC50 |
|---|---|---|
| 1 | 9.0 | 7.6 |
| 2 | 8.0 | 6.8 |
| 3 | 8.3 | 7.3 |
| 4 | 8.7 | 6.8 |
| 5 | 6.0 | 5.5 |
| 6 | 8.1 | 7.1 |
| 7 | 6.0 | 5.9 |
| 8 | 9.5 | 6.7 |

D. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I),

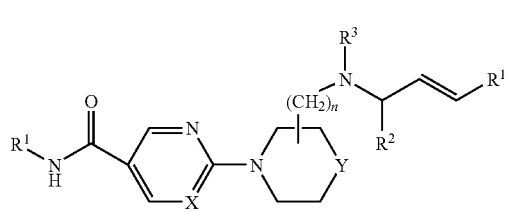

(I)

the N-oxide forms, the pharmaceutically acceptable addition salts and the stereo-chemically isomeric forms thereof, wherein X is N;

Y is independently CH or $CH_2$ and when Y is CH then a substituent of CH is attached to the Y atom of the ring structure;

n is 0 or 1 and when n is 0 than a direct bond is intended;

$R^1$ is phenyl, or naphtalenyl; wherein each of said phenyl or naphtalenyl is optionally substituted with one or two substituents each independently selected from halo, $C_{1-6}$alkyl, $C_{1-6}$alkyloxy, polyhalo$C_{1-6}$alkyl, aryl, hydroxy, cyano, amino, $C_{1-6}$alkylcarbonylamino, $C_{1-6}$alkylsulfonylamino, hydroxycarbonyl, $C_{1-6}$alkyloxycarbonyl, hydroxy$C_{1-6}$alkyl, $C_{1-6}$alkyloxymethyl, aminomethyl, $C_{1-6}$alkylaminomethyl, $C_{1-6}$alkylcarbonylaminomethyl, $C_{1-6}$alkylsulfonylaminomethyl, aminosulfonyl, $C_{1-6}$alkylaminosulfonyl or heterocyclyl;

$R^2$ is —$CH_2$—$R^5$, trifluoromethyl, —C(=O)—$R^6$, or —$CH_2$—$NR^7R^8$; wherein each $R^5$ is independently selected from hydrogen, hydroxy, $C_{1-6}$alkyloxy, piperazinyl, N-methylpiperazinyl, morpholinyl, thiomorpholinyl, imidazolyl or triazolyl;

each $R^6$ is independently selected from hydroxy, $C_{1-6}$alkyloxy, amino or mono- or di($C_{1-6}$alkyl)amino, $C_{3-6}$cycloalkylamino, piperazinyl, N-methylpiperazinyl, morpholinyl or thiomorpholinyl;

each $R^7$ and $R^8$ are independently selected from hydrogen, $C_{1-6}$alkyl, $C_{1-6}$alkylcarbonyl, $C_{1-6}$alkylsulfonyl, or mono-or di($C_{1-4}$alkyl)aminosulfonyl;

$R^3$ is hydrogen, $C_{1-6}$alkyl, cyano$C_{1-4}$alkyl, $C_{1-6}$alkyloxycarbonyl, hydroxy$C_{1-6}$alkyl, $C_{1-6}$alkyloxy$C_{1-6}$alkyl, $C_{3-6}$cycloalkyl, $C_{3-6}$cycloalkyl$C_{1-6}$alkyl, aryl$C_{1-6}$alkyl, $C_{1-6}$alkylcarbonyl, $C_{1-6}$alkylsulfonyl;

$R^4$ is hydroxy.

2. A compound as claimed in claim 1 wherein each X is N; Y is CH; $R^1$ is phenyl; $R^2$ is —$CH_2OH$ or methyl; $R^3$ is hydrogen, $C_{1-6}$alkylcarbonyl or $C_{1-6}$alkylsulfonyl.

3. A compound as claimed in claim 1 wherein each X is N; each Y is CH; n is 1; $R^1$ is phenyl; $R^2$ is —$CH_2OH$ or methyl;

$R^3$ is hydrogen or $C_{1-6}$alkylsulfonyl; and $R^4$ is hydroxy.

4. A compound selected from the group consisting of:

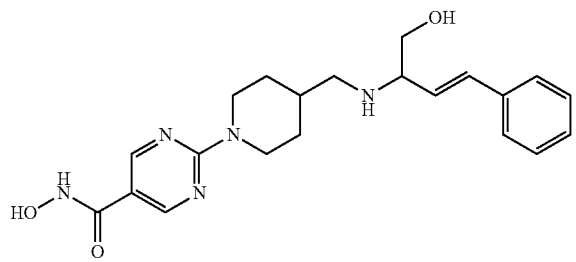

Compound No 1

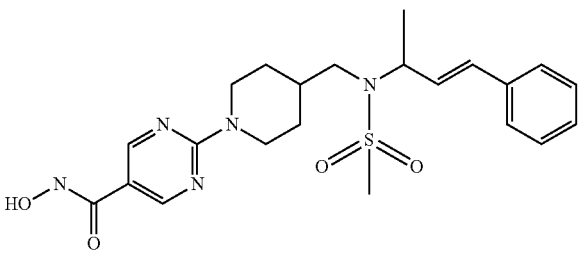

Compound No 8 and the N-oxide forms, the pharmaceutically acceptable addition salts and the stereo -chemically isomeric forms thereof.

5. A pharmaceutical composition comprising pharmaceutically acceptable carriers and as an active ingredient a therapeutically effective amount of a compound as claimed in claim 1.

6. A process of preparing a pharmaceutical composition comprising mixing a pharmaceutically acceptable carrier and the compound as claimed in claim 1.

7. A combination of an anti-cancer agent and a compound as claimed in claim 1, wherein the compound of claim 1 is a HDAC inhibitor.

8. A process for preparing a compound as claimed in claim 1, comprising a) reacting an intermediate of formula (II) with an appropriate acid, yielding a compound of formula (I), wherein $R^4$ is hydroxy, herein referred to as a compound of formula (I-a), or

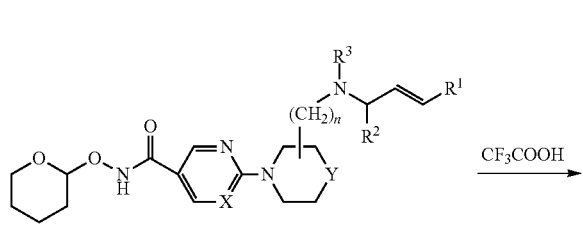

(II)

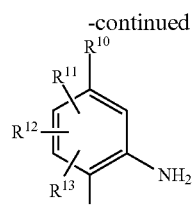

(IV)

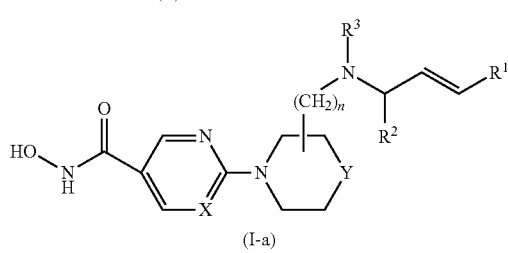

(I-a)

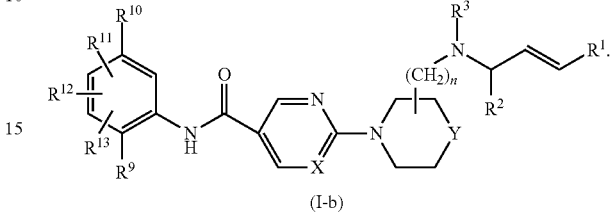

(I-b)

b) reacting an intermediate of formula (III) with an intermediate of formula (IV) wherein M represents hydrogen, or sodium, lithium or an alkali metal cation, in the presence of appropriate reagents, yielding a compound of formula (I), wherein $R^4$ is a radical of formula (a-1) and $R^9$ is —$NH_2$, herein referred to as a compound of formula (I-b)

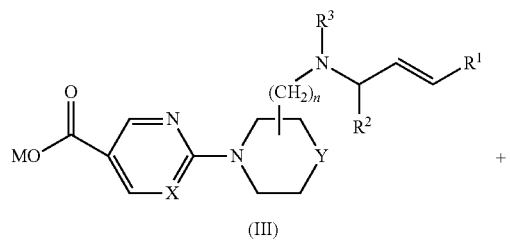

(III)

9. A pharmaceutical composition comprising pharmaceutically acceptable carriers and as an active ingredient a therapeutically effective amount of a compound as claimed in claim 2.

10. A pharmaceutical composition comprising pharmaceutically acceptable carriers and as an active ingredient a therapeutically effective amount of a compound as claimed in claim 3.

11. A pharmaceutical composition comprising pharmaceutically acceptable carriers and as an active ingredient a therapeutically effective amount of a compound as claimed in claim 4.

12. A combination of an anti-cancer agent and a compound as claimed in claim 2, wherein the compound of claim 2 is a HDAC inhibitor.

13. A combination of an anti-cancer agent and a compound as claimed in claim 3, wherein the compound of claim 3 is a HDAC inhibitor.

14. A combination of an anti-cancer agent and a compound as claimed in claim 4, wherein the compound of claim 4 is a HDAC inhibitor.

\* \* \* \* \*

UNITED STATES PATENT AND TRADEMARK OFFICE
CERTIFICATE OF CORRECTION

PATENT NO. : 8,138,198 B2  
APPLICATION NO. : 11/914208  
DATED : March 20, 2012  
INVENTOR(S) : Patrick René Angibaud et al.

Page 1 of 2

It is certified that error appears in the above-identified patent and that said Letters Patent is hereby corrected as shown below:

In the Claims

Column 49,  
Claim 1, lines 30-39,

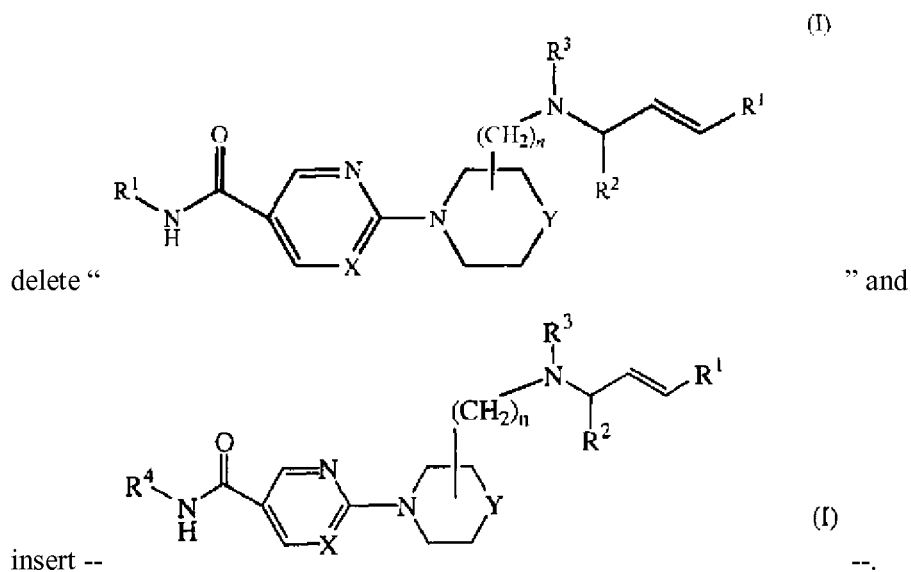

delete " " and insert -- --.

Signed and Sealed this  
Eighteenth Day of February, 2014

Michelle K. Lee  
*Deputy Director of the United States Patent and Trademark Office*

CERTIFICATE OF CORRECTION (continued)

U.S. Pat. No. 8,138,198 B2

Column 50,
Claim 4, lines 37-47, delete " 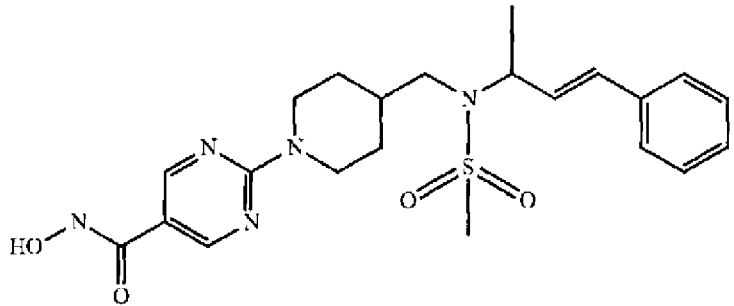 " and insert -- 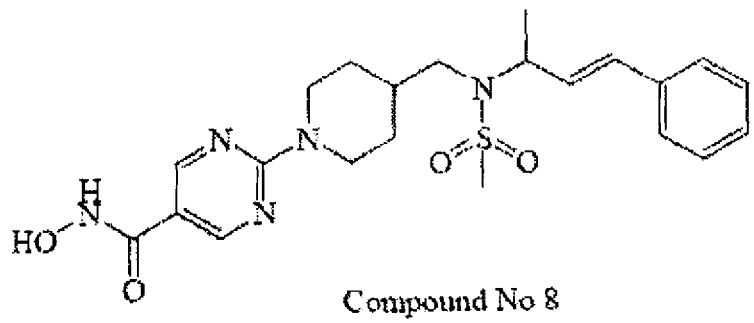 --.

Column 52,
Claim 8, lines 11-18, delete " 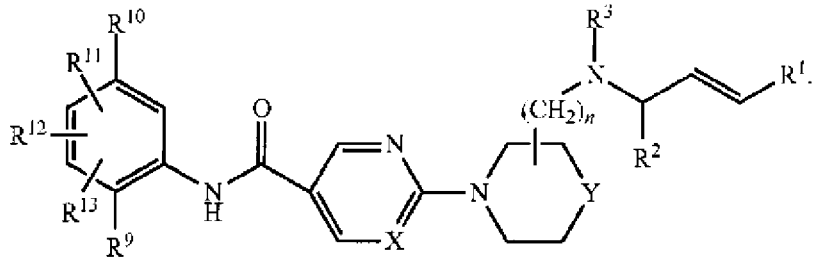 " and insert -- 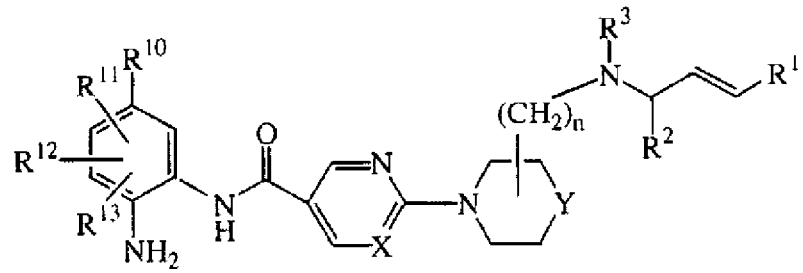 --.